United States Patent [19]

Logan

[11] 4,201,093
[45] May 6, 1980

[54] ULTRASONIC SHEET MATERIAL TESTING APPARATUS

[75] Inventor: James D. Logan, Pullman, Wash.

[73] Assignee: Metriguard, Inc., Pullman, Wash.

[21] Appl. No.: 926,702

[22] Filed: Jul. 20, 1978

[51] Int. Cl.² ............................................. G01N 29/00
[52] U.S. Cl. ...................................... 73/618; 73/609
[58] Field of Search ................. 73/609, 610, 618, 632, 73/633, 635, 639, 641, 642, 644

[56] References Cited

U.S. PATENT DOCUMENTS

| | | | |
|---|---|---|---|
| 3,233,449 | 2/1966 | Harmon | 73/642 |
| 3,262,123 | 7/1966 | Crouch | 73/610 |
| 3,612,920 | 10/1971 | Bantz | 73/639 |
| 3,628,375 | 12/1971 | Pagano | 73/639 |
| 3,720,098 | 3/1973 | Dixon | 73/609 |
| 3,745,813 | 7/1973 | Uozumi | 73/639 |
| 3,780,570 | 12/1973 | Collins | 73/618 |
| 3,808,879 | 5/1974 | Rogers | 73/609 |
| 3,908,446 | 9/1975 | Mruk | 73/642 |
| 3,938,371 | 2/1976 | Dini | 73/633 |
| 3,938,372 | 2/1976 | Sproule | 73/633 |
| 3,962,908 | 6/1976 | Joy | 73/636 |

OTHER PUBLICATIONS

G. L. Gooberman, "Ultrasonics Theory and Application," English Universities Press Ltd., p. 111, 1968.

*Primary Examiner*—Stephen A. Kreitman
*Attorney, Agent, or Firm*—Klarquist, Sparkman, Campbell, Leigh, Hall & Whinston

[57] ABSTRACT

A device for testing sheet material, such as wood veneer, includes a rolling transducer for introducing ultrasonic signals into the veneer so as to cause travel of the signals generally in the plane of the veneer. Coupling oil filling this transducer facilitates the transmission of the signals into the veneer. Another similar rolling transducer is provided to detect the travelling ultrasonic signals. Each rolling transducer includes a special rim with an annular focusing ring for directing the ultrasonic signals to and from the veneer. A timer circuit produces a signal representing the travel time taken for an ultrasonic signal to pass between the transducers. An averaging circuit obtains an average of such travel times for each sheet and a grading circuit causes the sheet to be marked with a grade corresponding to the average travel time. A signal threshold detector prevents travel times for detected signals of a magnitude less than a preselected minimum level from being included in the average. Travel times for detected signals of a magnitude exceeding a noise level are blocked by a noise discriminator from being averaged. A variable noise level circuit adjusts the magnitude of the noise level at certain times following the transmission of an ultrasonic signal into the veneer. Detected signals having a travel time which is not between a preselected minimum and maximum time established by a time window circuit are disregarded. A calibration signal generator provides a signal of a known and adjustable time length for use in adjusting the grade corresponding to travel times.

28 Claims, 12 Drawing Figures

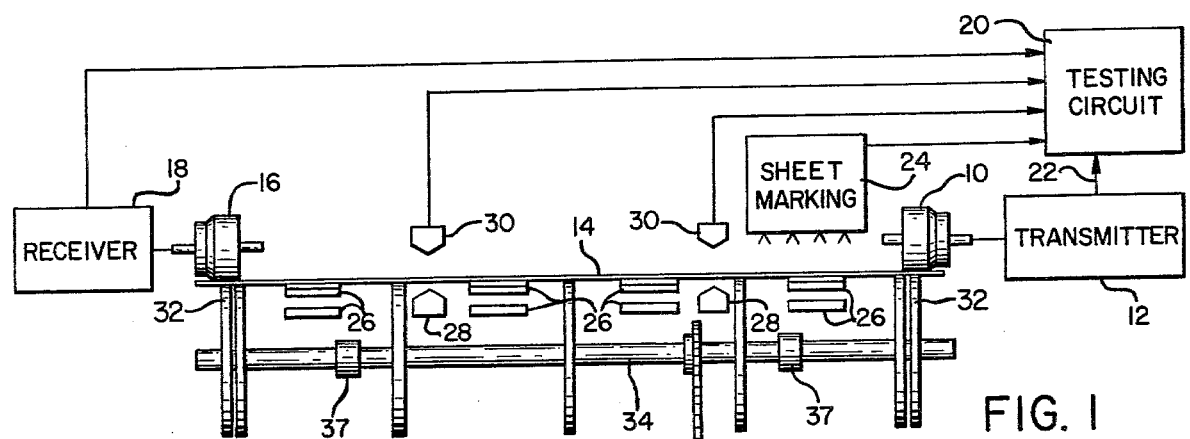
FIG. 1
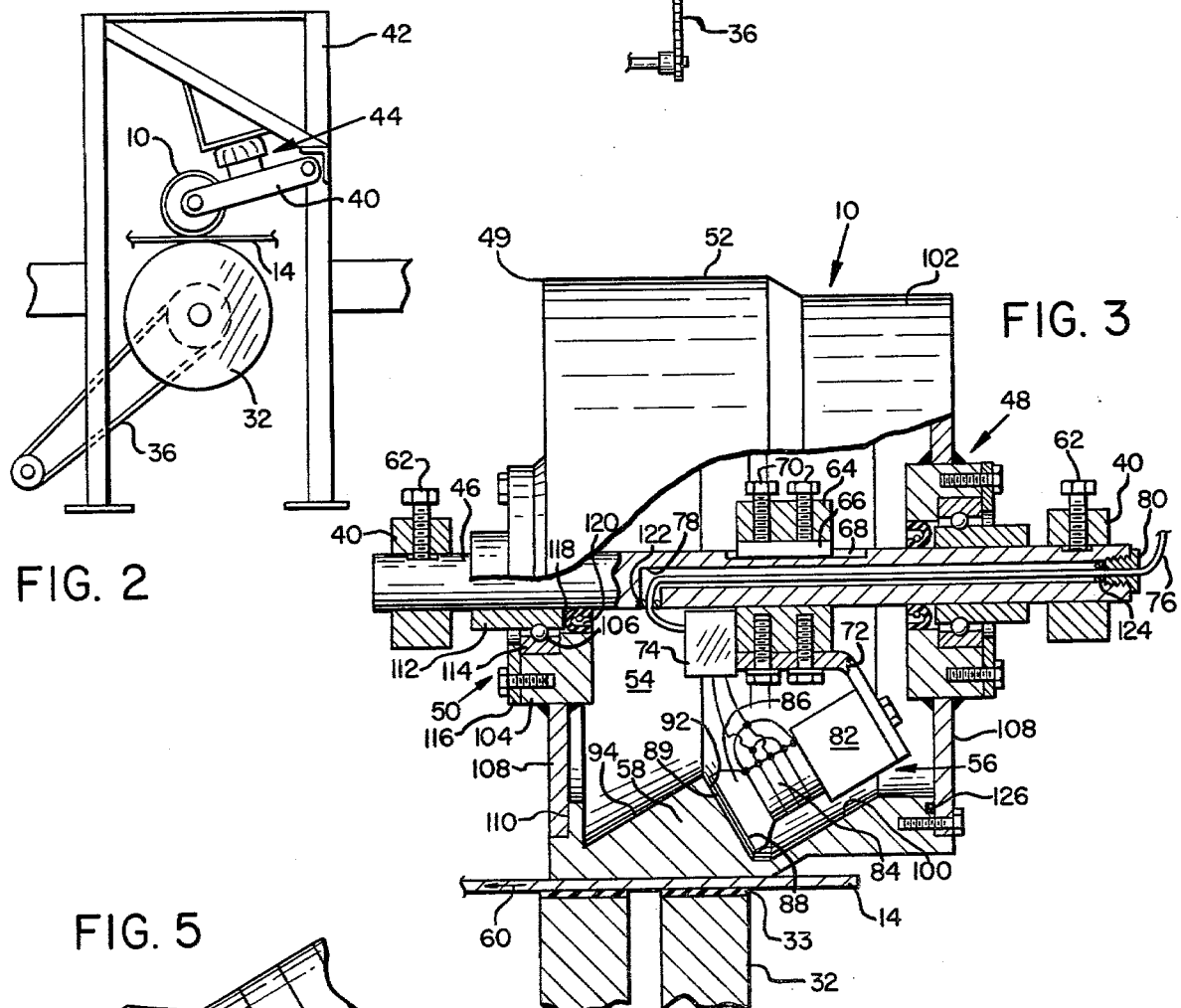
FIG. 2
FIG. 3
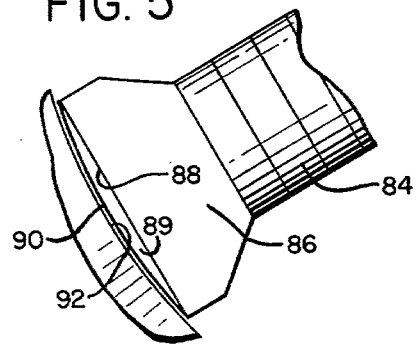
FIG. 5

| | |
|---|---|
| 12a | AC SOURCE |
| 12b | ACO |
| 12c | RANGE GATE A Q OUTPUT |
| 12d | RANGE GATE B Q OUTPUT |
| 12e | TIME WINDOW |
| 12f | WAIT TO ADD TO AVERAGE |
| 12g | ETI |
| 12h | VALID SIGNAL |
| 12i | SIGNAL |
| 12j | REFERENCE |
| 12k | AVERAGE |

1

ULTRASONIC SHEET MATERIAL TESTING APPARATUS

BACKGROUND OF THE INVENTION

1. Field of the Invention

The present invention relates to ultrasonic sheet material testing devices, and more particularly to ultrasonic rolling transducers and to testing devices of the type which measure the time taken by an ultrasonic signal to travel through a length of the sheet material.

2. Description of the Prior Art

A number of prior art rolling contact ultrasonic transducers are known. However, none of these rolling transducers are capable of introducing ultrasonic signals into sheet material for travel generally in the plane of the material from the location of entry to another location. Therefore, they cannot be used in a device which measures the travel time of an ultrasonic signal along a length of sheet material for use in quality testing the material. An example of a typical known rolling transducer is shown in U.S. Pat. No. 3,628,378 of Pagano. In Pagano, ultrasonic signals are transmitted from a transducer in directions normal to, or offset somewhat from normal to, the surface of a test material so that they are reflected back from the material. Echoes of the transmitted signals returning to the transducer are then displayed on a cathode ray tube oscilloscope.

In many industrial plants, sheet material is graded by an employee who watches the material as it passes by on a conveyor. This method of grading is highly inaccurate since the visually-observable characteristics relate poorly to mechanical properties of the material. Factors affecting accuracy include the fatigue of the employee, limitations on the ability of the employee to discover concealed flaws such as hairline cracks and internal defects, the experience of the employee, and the speed at which the sheet material is conveyed.

In an effort to make sheet material testing more accurate, one prior art device introduces stress waves into a sheet of particleboard using a mechanical impactor clipped to one end. A sensor clipped to the other end of the sheet receives these waves and the time taken for the waves to travel through the sheet is indicated on a meter. Although in some instances this type of device will produce a quality indication which is more accurate than can be obtained by an employee using the above approach, it is extremely time consuming. That is, the impactor and sensor are first manually clipped to a stationary panel and a time measurement is obtained. To take another reading on the same panel, or on another panel, these clipped elements must be moved. Because of the time required to take each measurement, it is not feasible to take more than a relatively few measurements for each panel. As a result, accuracy suffers as flaws that do not happen to be in the path of a stress wave won't be detected. More importantly, it would be impractical to try and clip the sensor and the impactor to sheet material moving on a conveyor. Furthermore, this type of device is monitored by an operator who compares a measured stress wave travel time measurement with a known standard travel time. For this reason, operator fatigue and the other factors mentioned above also affect overall accuracy and suitability as a testing system.

Accordingly, there is a need for a rolling contact transducer capable of accurately focusing ultrasonic waves into sheet material for travelling in the sheet and for such a transducer which detects ultrasonic signals travelling in the sheet. There is also a need for an ultrasonic testing device which measures the travel time of ultrasonic signals through a length of sheet material and uses these measurements in grading the sheet.

SUMMARY OF THE INVENTION

The present invention provides a transmitter rolling ultrasonic transducer capable of introducing ultrasonic signals into sheet material for travel generally in the plane of the sheet. A similar receiver rolling transducer is also provided for detecting such travelling ultrasonic signals. The time taken by the ultrasonic signals to travel between the transducers is measured by a testing circuit and used for grading the sheet.

One feature of the rolling transducers is a special focusing ring for coupling ultrasonic signals between an ultrasonic transducer within the rolling transducers and the plane of the sheet material.

As still another feature of the invention, the rolling transducers have a rim with a contacting surface for rolling on the sheet material, the focusing ring rotates past the ultrasonic transducer when the rim rolls, and the ring is positioned so that the ultrasonic transducer is continuously ultrasonically coupled to the sheet material through the contacting surface by a portion of the ring.

Another feature of the rolling transducers is a recessed rim portion which reduces the amount of conveyor noise detected by the rolling transducers.

As a more specific feature of the invention, the focusing ring includes an annular focusing surface positioned so that a portion of this surface is parallel to and spaced from a focusing surface of the ultrasonic transducer during rolling of the rim.

As a further feature of the invention, the plane of the sheet material and a line perpendicular to the transducer focusing surface intersect at an angle which facilitates passage of the ultrasonic signals into and out of the sheet material.

As another feature of the invention, the focusing ring is of right triangular cross section with its hypotenuse positioned parallel to the plane of the sheet material and its base contained in the annular focusing surface.

An additional feature of rolling transducers is an annular notch oriented for positioning of the transducer therein.

As another feature of the invention, the rolling transducers are filled with coupling oil and the oil for the transmitter rolling transducer is specially treated so as to reduce cavitation of the oil in the space between the annular focusing surface and the transducer focusing surface when the oil is subjected to intense ultrasonic energy.

Yet another feature of the rolling transducers is a submersible transformer located within the transmitter rolling transducer for applying a high voltage pulse to the ultrasonic transducer so as to cause generation of ultrasonic signals.

One broad feature of the testing circuit of the invention is circuitry for measuring the travel time of ultrasonic signals in sheet material between the rolling transducers.

Another feature of the testing circuit is a threshold detector for rejecting signals detected by the receiver rolling transducer which are of insufficient magnitude to have arisen from a transmitted ultrasonic signal travelling through the sheet.

An additional feature of the testing circuit is a noise discriminator for differentiating noise detected by the receiver rolling transducer from detected ultrasonic signals travelling from the transmitter rolling transducer.

A feature of the noise discriminator is a variable noise level generator which adjusts the magnitude of the noise threshold voltage level as a function of time measured from the transmission of an ultrasonic signal into the sheet.

Another feature of the testing circuit is a time window circuit for establishing a preselected and adjustable minimum and maximum expected time for ultrasonic signals to travel between the transducers, and which causes detected signals outside these minimum and maximum travel times to be disregarded.

A further feature of the testing circuit is a timer circuit for measuring the travel time of ultrasonic signals transmitted through a length of sheet material and for producing a voltage representation of these travel times.

Still another feature of the testing circuit is an averaging circuit which averages the individual measurements of travel times to produce an overall average travel time signal for a sheet, this overall average being representative of the grade of the sheet material.

Another feature of the testing circuit is a grading circuit with adjustable grade threshold circuits responsive to the overall average travel time signals so as to control the marking of a grade on the sheet corresponding to the overall average.

A further feature of the testing circuit is a calibration signal generator for producing signals of known and adjustable length for use in adjusting the grade thresholds to desired settings.

It is one object of the present invention to provide a rolling transmitter transducer capable of transmitting ultrasonic signals into a sheet of material for travel in the plane of the sheet.

It is an additional object of the invention to provide a rolling contact receiver transducer capable of detecting ultrasonic signals travelling in the plane of sheet material.

Another object of the invention is to provide a rolling transducer in which the major parts are interchangable as a transmitter for introducing ultrasonic signals into the sheet material and as a receiver for detecting ultrasonic signals travelling in the sheet material.

Another object is to provide rolling transducers which minimize the effects of noise on their operation.

A further object of the present invention is to provide an improved rolling contact transducer which is of simple construction, requires low maintenance, accurate, and which is reliable.

Another object of the invention is to provide a device for accurately measuring the time taken by ultrasonic signals to travel through a length of sheet material.

A further object of the present invention is to provide an ultrasonic sheet material testing device for automatically grading sheet material which is moving, such as on a conveyor belt.

Another object of the invention is to provide a device which averages the time taken by a plurality of successive ultrasonic signals to travel through a length of a sheet of material.

An additional object is to provide a device which discriminates detected ultrasonic signals transmitted into a sheet of material for testing purposes from detected signals originating from other sources, such as conveyor belt noise.

A further object of the invention is to provide a sheet material testing device for increasing the productivity of a plant by reducing errors and labor spent in grading sheet material.

The foregoing objects, features, and advantages of the present invention will become more apparent from the following detailed description, which proceeds with reference to the accompanying drawing.

BRIEF DESCRIPTION OF THE DRAWING

In the drawing:

FIG. 1 is a front view, partially in block diagram form, of an ultrasonic testing apparatus in accordance with the present invention;

FIG. 2 is a side elevation view of the apparatus of FIG. 1;

FIG. 3 is a partially broken away elevation view of the transmitter rolling transducer of FIG. 1;

FIG. 5 is an enlarged view of a portion of the rolling transducer taken looking down in FIG. 3 in a direction generally parallel to the lowermost element of a frustoconical transducer focusing surface in the interior of the transducer.

DESCRIPTION OF THE PREFERRED EMBODIMENT

General Arrangement

Figure 7:
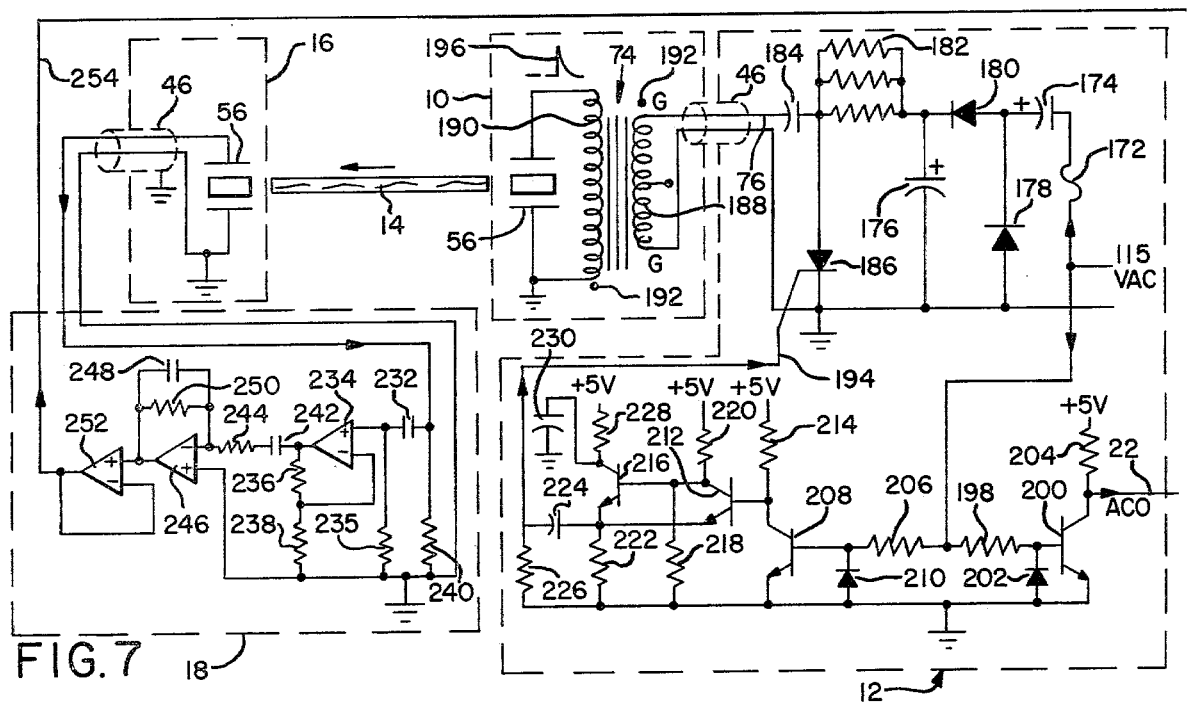
FIG. 7 is an electrical schematic diagram of the transmitter and receiver of FIG. 6.

As shown in FIG. 1, one embodiment of an ultrasonic sheet material testing apparatus of the invention includes a rolling transducer 10 driven by a transmitter 12 for introducing ultrasonic signals into sheet material 14. These introduced signals travel generally in the plane of the sheet from transducer 10 to another rolling transducer 16 which detects them. A receiver 18 connected to an output of rolling transducer 16 produces an output signal representing the detected signals and transmits this output to an input of a testing circuit 20. A synchronizing signal from transmitter 12 is fed to testing circuit 20 on a line 22. This signal occurs each time that the transmitter causes rolling transducer 10 to transmit an ultrasonic signal into the sheet material. By measuring the time between the receipt of a synchronizing signal and of a receiver output signal, testing circuit 20 determines how long it took for an ultrasonic signal to travel through a length of the sheet material. From a plurality of such measured travel times for each sheet, testing circuit 20 causes a sheet marking apparatus 24 to mark the sheet with an appropriate grade.

Because such travel times vary with characterstics affecting quality of the sheet material, variations in travel time indicate differences in quality, and can be used to grade the material. Although the present invention may be used to test many types of sheet materials, it is particularly suitable for testing material containing wood fibers, such as paper, particle board, lumber and wood veneers. It is to be understood that the term sheet material is not limited to products containing wood fiber. However, this description proceeds with reference to the specific example of testing dry wood veneer by directing ultrasonic signals along the grain direction of the veneer. Furthermore, the specific example refers to rolling transducers positioned 93 inches apart. Of course, the invention is suitable for testing materials of varying lengths. Factors affecting travel time of signals through the veneer include such things as the integrity of the sheet (i.e. the presence of cracks, knotholes, etc.) in the path of travel of the signals and the presence of diving grain. Diving grain refers to wood grain which is not parallel with the plane of the sheet.

Wood veneer is carried to a test zone between transducers 10 and 16 by endless conveyor belts 26. Just prior to entering the test zone, the veneer breaks light beams passing between photosensor transmitters 28 and photosensor receivers 30. When this occurs, the photosensor receivers send a signal to the testing circuit to indicate that the veneer is ready to enter the test zone. Upon reaching the test zone, press wheels 32, mounted to a shaft 34 and driven by a chain drive 36 coupled to a motor (not shown) carry the veneer past the rolling transducers. It is not unusual for the veneer to travel past the transducers at a rate of around one to two hundred feet per minute. Press wheels 32 are typically coated with a polyurethane material 33, in FIG. 3, to reduce the transmission of noise from the press wheels and the driving mechanism. In addition, shaft 34 is segmented with the segments joined together by rubber couplers 37 to reduce conveyor noise travelling from one end of the shaft to the other.

As shown in FIG. 2, each rolling transducer 10, 16 is mounted between a pair of transducer support arms 40 at one end of these arms. The arms are in turn pivoted at their other end to a frame 42. An air bag assembly 44 associated with each rolling transducer presses upwardly against a portion of frame 42 and provides a compliant downward force on arms 40 to in turn urge the rolling transducers against the veneer. The magnitude of the compliant force is adjustable by a pneumatic pressure regulator (not shown). The outer most press wheels 32 are positioned beneath the rolling transducers to reinforce the veneer against the compliant force. With this construction, a solid contact is continuously maintained between the rolling transducers and the veneer.

Rolling Transducers

Referring to FIG. 3, rolling transducer 10 includes an axle or shaft 46 rotatably supporting a roll. The roll comprises a pair of spaced apart similar hub assemblies 48, 50 and a cylindrical rim 49 having an outer peripheral contacting surface 52 which rolls in contact with veneer sheet 14. The rim is supported at its ends by the outer peripheral edge portions of the respective hub assemblies 48, 50. The interior surface of the rim together with the interior surfaces of the hub assemblies define a transducer chamber 54 within the roll. A transducer assembly 56, positioned in chamber 54, converts electrical energy into ultrasonic signals. Transducer assembly 56 directs these signals through a focusing portion 58 of the rim 49 so that the ultrasonic signals are directed into the sheet material generally in the direction indicated by an arrow 60.

Shaft 46 is of a simple, rigid, one piece construction, preferably of tool steel, and is secured at its ends to the respective arms 40 by set bolts 62. An annular collar 64 is secured to shaft 46 at a position intermediate the hub assemblies 48, 50. A key 66 disposed in a key way 68 of the shaft and in another key way of the collar prevents the collar from rotating. Set bolts 70 prevent movement of the collar axially along the shaft. Transducer assembly 56 is bolted to an angle bracket 72 which in turn is bolted to collar 64. Because of this rigid mounting, the transducer assembly is continuously maintained in a desired orientation relative to the focusing portion 58 to thereby facilitate the transfer of ultrasonic energy into veneer sheet 14.

Electrical pulses from a submersible or potted transformer 74, mounted to collar 64, energizes the transducer assembly 56 causing it to produce ultrasonic signals. Electrical energy is conducted to the transformer from transmitter 12 by a coaxial cable 76 extending through a passageway 78 in the shaft 46. The voltage of the pulses from transformer 74 is on the order of five kilovolts. Hence, with transformer 74 positioned within transducer chamber 54, these pulse voltages can be obtained without exceeding the insulation voltage limitations of a relatively small sized cable 76, since this cable can carry signals of a much lower voltage than the pulses presented to the transducer. Passageway 78 extends from one end of the shaft, along its axis, to a point between collar 64 and hub assembly 50 and then radially outwardly to transducer chamber 54. A threaded plug 80 caps this passageway at the point where it leaves the end of the shaft and is provided with an axial hole through which conductor 76 passes.

Transducer assembly 56 includes a conventional steel backing mass 82 adjacent to bracket 72, multiple piezoceramic or piezoelectric wafers 84 and a front mass 86 positioned between the wafers and the focusing portion 58 of the rim 49. Steel mass 82 helps tune the transducer assembly to a proper resonance frequency. In one preferred embodiment the resonance frequency typically falls in the range of from twenty three to twenty-seven kilohertz. The wafers are electrically connected to transformer 74 in a well known manner and comprise commercially available ultrasonic piston transducers which may be of the lead zirconate titanate type. The front mass 86 has a generally rectangular planar surface 88 through which ultrasonic signals are transmitted. This surface is coated with an epoxy layer 89 (FIG. 5) which has a curved outer surface 90 to provide a coupling surface which is parallel to an adjacent frustonconical surface on focusing portion 58 as explained below.

Figure 4:
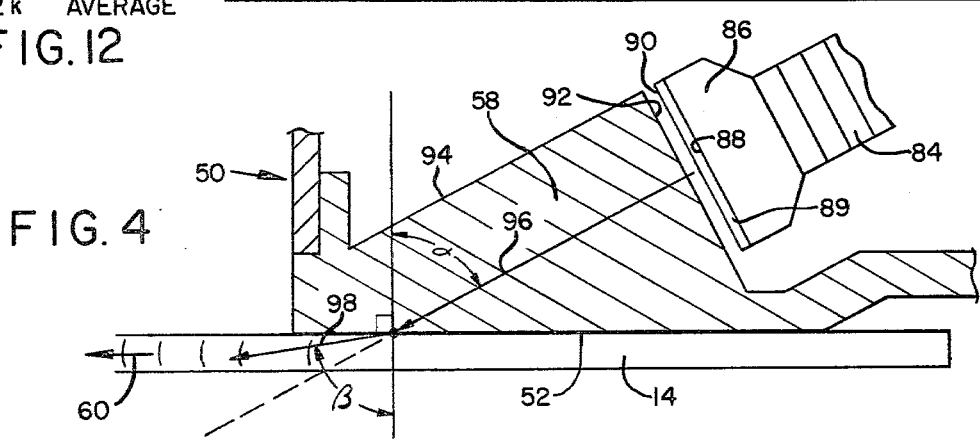
FIG. 4 is an enlarged vertical section of a portion of the rolling transducer of FIG. 3.

Focusing portion 58, as shown in FIG. 4, comprises an annular focusing ring which extends radially inwardly from the contacting surface 52 of the rim. This ring has the frustoconical coupling surface 92 formed thereon which surface is parallel to and spaced from the transducer coupling surface 90. A uniform gap of about twenty to fifty thousandths of an inch or smaller is established between these two surfaces so that, as the wheel rotates, surface 92 on focusing portion 58 moves past the stationary transducer coupling surface 90. FIG. 5 shows in greater detail the coating 89 on the front mass surface 88. This coating is applied to surface 88 so that the transducer coupling surface 90 follows the contour of frustoconical coupling surface 92 to thereby provide the uniform gap. The annular focusing ring is of generally right triangular cross section with a hypotenuse parallel to the contacting surface 52, a base contained in the surface 92, and a leg 94 perpendicular to surface 92. Transducer assembly 56 is oriented so that a projection of the surface 88, in a direction perpendicular to this surface, passes generally through focusing portion 58 and the rim 49 contacting surface 52 which is rolling on the veneer.

Ultrasonic signals from transducer assembly 56 travel primarily in a direction perpendicular to coupling surface 90, as indicated by arrow 96 (FIG. 4) to the surface of the sheet material 14. Upon entry into the veneer, the waves bend to travel along a line 98 and eventually travel in the plane of the sheet as shown by arrow 60. The angle $\alpha$, is the angle of incidence between the primary direction of travel 96 of the ultrasonic pressure waves in the focusing portion 58 and a line normal to the horizontal upper surface of the veneer. Angle $\alpha$ is established by the shape and material of focusing portion 58 and the orientation of transducer assembly 56. Furthermore, angle $\alpha$ is selected so that significant portions of the generated ultrasonic signals are not reflected off the interface between the rim 52 of the wheel and the upper surface of the sheet material. In other words, $\alpha$ is selected so that $\beta$, the angle of refraction is slightly less than 90 degrees. The material forming the focusing portion is preferably such that the speed of travel of ultrasonic signals through this material is slower than the speed of travel in the sheet. Consequently, the ultrasonic signals will bend toward the horizontal upon entering the veneer. Aluminum and magnesium are examples of suitable materials for a focusing portion 58 for use in testing wood veneer sheets in an application wherein ultrasonic signals travel along the plane of the sheet. Other materials would be suitable for other applications.

With an aluminum focusing portion, angle $\alpha$ is established within a range of from fifty to seventy degrees for satisfactory entry of ultrasonic signals into the veneer. More specifically, $\alpha$ is preferably set at sixty degrees to maximize the passage of ultrasonic signals through focusing portion 58 and into the sheet for travel along the plane of the veneer.

Referring again to FIG. 3, transducer assembly 56 nests within a portion of an annular notch in the rim. This notch is bounded on one side by the frustoconical surface 92 and along its other side by a surface 100 which is generally parallel to surface 94. Clearance is provided between surface 100 and transducer 56 so that the wheel can rotate without the rim contacting the transducer. This notch provides room within transducer chamber 54 for mounting transducer 56 with the coupling surface 90 in proper relationship to the focusing ring surface 92.

The rim 49 also has a section 102 of reduced diameter between hub assembly 48 and the piezoelectric wafer size of front mass 86. Because of this reduced diameter, a recessed portion of the roll is formed with rim section 102 not rolling in contact with veneer 14. As a result, conveyor acoustical noise that otherwise might be transmitted to the rolling transducer from the sheet through rim section 102 is reduced. This recess is particularly advantageous in the receiver rolling transducer wherein it is desirable to reduce the detection of extraneous signals.

Hub assemblies 48, 50 are generally identical with the exception that assembly 48 is bolted to the rim so that it can be readily removed for recess to the transducer chamber. Because of this similarity, only hub assembly 50 will be described. Assembly 50 includes a central hub 104 rotatably mounted by a ball bearing 106 to shaft 46. An annular plate 108; perpendicular to the axis of shaft 46, is mounted to central hub 104. The outer peripheral edge of plate 108 is received in an annular recess 110 of the rim. The inner bearing race 112 of bearing 106 is secured to shaft 46 and the outer bearing race 114 is held in an annular channel bounded on one side and at its base by central hub 104 and at its other side by a bearing retainer plate 116 secured to the central hub. Epoxy glue is used to secure plate 108 to the central hub and to the rim so that stress concentrations are reduced and the joints are sealed. An annular seal receiving recess 118 opens inwardly toward transducer chamber 54 and is bounded at its base by the inward end of inner bearing race 112, at one side by shaft 46 and at its other side by a portion of central hub 104. A lip seal 120 positioned within recess 118 prevents leakage of fluid from chamber 54 through bearing 106.

Similarly, O-ring seals 122, 124 positioned at opposite ends of passageway 78 seal the transducer chamber at these points. Also, an additional O-ring seal 126 is positioned between plate 108 of the removable hub assembly 48 and the rim to further seal the transducer chamber.

To improve the coupling between the transducer assembly 56 and the focusing ring portion 58, the transducer chamber 54 is filled with a coupling fluid such as oil. As mentioned above, transducer chamber 54 is sealed so that the coupling oil is not lost. This oil is of a type having a low vapor pressure of under 1 mm mercury at 120° F. The use of a low vapor pressure oil minimizes cavitation and resultant bubble formation in the gap between the transducer 56 and focusing portion 58 arising from the generation of ultrasonic signals by the transducer. Such bubbles would absorb ultrasonic energy and impede the transmission of sufficient ultrasonic energy into the veneer for testing purposes. It has been experimentally determined that Duo-Seal vacuum pump oil manufactured by Sargent-Welch Scientific Company is suitable after it has been treated by a high temperature outgassing process. To start this process, the oil is first heated to approximately 250°-300° F. and a vacuum is applied. As a result, the oil emits gas. Further outgassing results from agitating the oil under vacuum conditions and leaving the oil under such conditions for a period of several hours.

The construction of the rim, shaft and hub assemblies of receiver rolling transducer 16 is identical to those of transmitter rolling transducer 10. However, a transformer 74 is not used in transducer 16. In addition, although the rolling transducer is preferably oil filled, cavitation of the oil is not a problem in the receiver rolling transducer because the intensity of the ultrasonic signals present in the gap between the focusing ring portion 58 and transducer 56 of the transmitter rolling transducer is much reduced. Hence, although convenient, a low vapor pressure oil is not needed in the receiver rolling transducer. Also, the transducer assembly 56 of receiver rolling transducer 16 must be capable of converting ultrasonic energy travelling in the plane of the veneer, and entering the rolling transducer through its focusing ring portion 58, into electrical signals which are then transmitted to the receiver 18 (FIG. 1).

Thus, many parts of the rolling transducers 10, 16 are readily interchangeable. As a result, they are easily manufactured because uniform machining and tooling can be employed.

TESTING CIRCUIT

General Arrangement

In general, successive ultrasonic signals are transmitted through the veneer sheet as it moves past the rolling transducers. The time taken for individual ultrasonic signals to travel between the transducers is measured and an average of these travel times is obtained for the veneer sheet. As the piece of veneer leaves the test zone, it is marked with a grade corresponding to the average travel time determined for the sheet.

Figure 6:
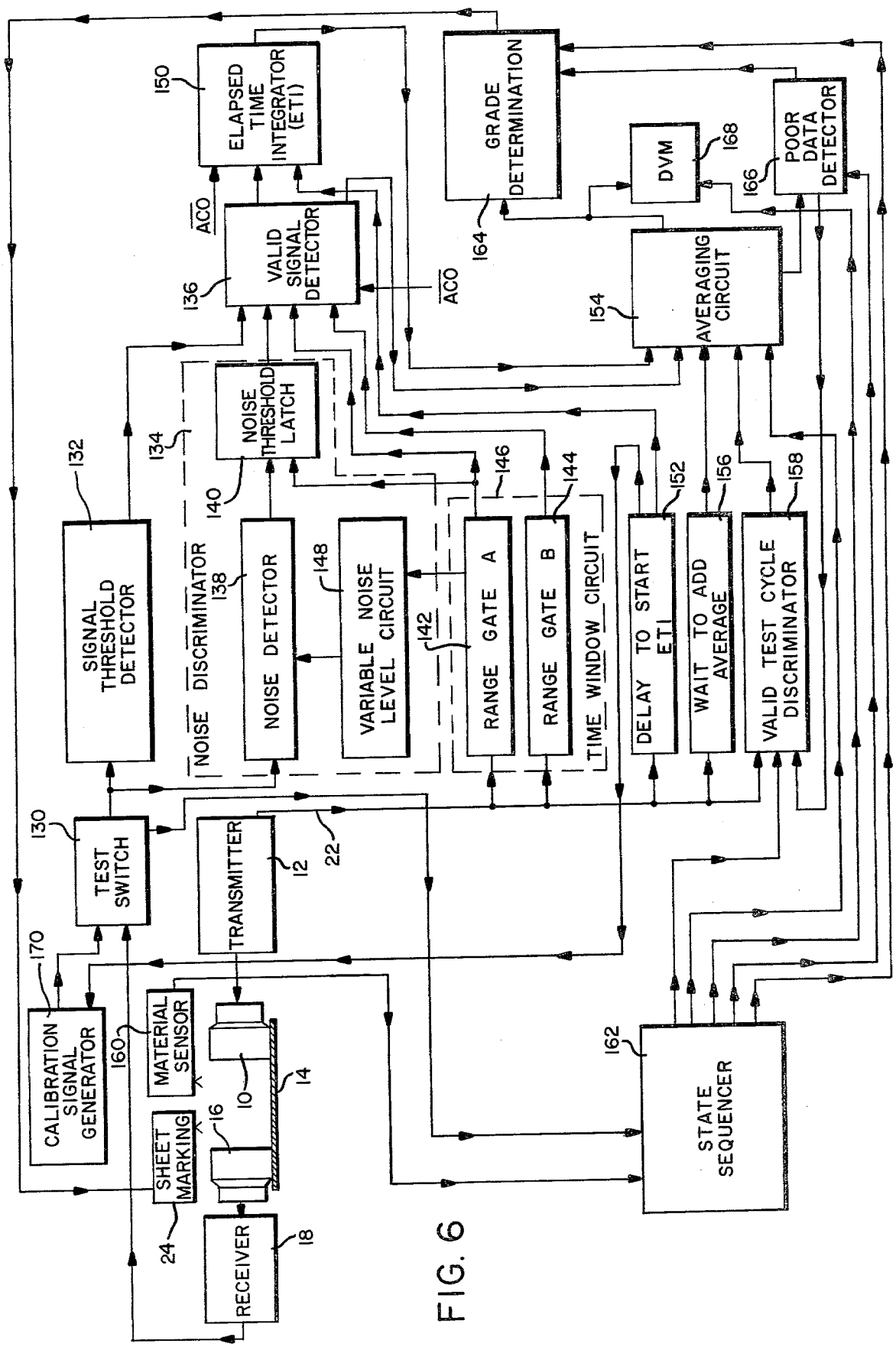
FIG. 6 is a block diagram of one form of an ultrasonic testing apparatus in accordance with the present invention.

More specifically, referring to FIG. 6, transmitter 12 causes rolling transducer 10 to introduce ultrasonic signals into veneer sheet 14. These signals travel along the sheet to rolling transducer 16, are converted to electrical signals and coupled to an input of receiver 18. Receiver 18 in turn produces an output representative of the detected ultrasonic signal. The receiver output is transmitted through a test switch 130 to inputs of a signal threshold detector 132 and a noise discriminator 134. Signal threshold detector 132 functions together with noise discriminator 134 and valid signal detector 136 to produce a valid signal indicating output as follows. This valid signal indicating output is generated whenever the receiver output exceeds a minimum magnitude expected to result when rolling transducer 16 detects an ultrasonic signal from the transmitter rolling transducer. Noise discriminator 134 includes a noise detector 138 for causing a noise threshold latch 140 to produce an invalid signal indication to an input of valid signal detector 136 whenever noise is detected. That is, the invalid signal is indicated when the receiver output signal is greater than expected when rolling transducer 16 detects an ultrasonic signal from rolling transducer 10.

Transmitter 12 produces a synchronizing signal ACO (FIG. 12) on line 126 at the same time it causes rolling transducer 10 to produce an ultrasonic signal. Thus, this ACO signal provides an indication of when an ultrasonic signal begins to travel through the veneer. The ACO signal is fed to inputs of a range gate 142 (Gate A) and a range gate 144 (Gate B) of a time window circuit 146. Time window circuit 146 establishes a minimum and maximum expected time for an ultrasonic signal to travel through a length of the veneer. The time window circuit sends signals to valid signal detector 136 indicating when the minimum and maximum times, measured from the negative-going edge of the ACO signal have been reached. The valid signal detector disregards, as invalid, those signals it receives that are not between these minimum and maximum times. Both these range gates are adjustable so that the time window may be adjusted to fit varying applications, such as testing differing types of sheet materials with different expected travel times. A variable noise level circuit 148, triggered by a signal from range gate 142, adjusts the noise detector so that the magnitude of signals it determines to be noise varies as a function of elapsed time from the negative-going edge of the ACO signal. In addition, range gate 142 resets noise threshold latch 140 with each ACO signal so that the noise detector indicates a valid signal until noise is detected.

At a time when detector 132 indicates a signal, during the time window, and when no noise has been detected, valid signal detector 136 produces a valid signal output to a timer, in this case an elapsed time integrator (ETI) 150. In its illustrated form, the ETI begins timing by integrating a voltage signal starting at a time delay from the negative-going edge of the ACO signal in response to a signal from a delay to start ETI circuit 152. The delay established by delay circuit 152 is of a duration equal to the constant time taken by the ultrasonic signals to pass between the transducer 56 of the respective rolling transducers 10, 16 and into the veneer. Thus, times measured by the ETI are of the time that an ultrasonic signal actually spends travelling in the veneer. ETI 150 continues integrating until it receives a valid signal from detector 136. Thereafter, the ETI holds the voltage it had reached at the time the valid signal was received.

The ETI output is fed to an input of an averaging circuit 154. However, to insure that each time measurement is given equal weight, a wait to add average circuit 156 delays the entry of each ETI output signal into the averaging circuit until after a constant delay time from the ACO signal. This delay time is selected to be longer than any expected propagation time of an ultrasonic signal through the veneer.

At times when averaging circuit 154 receives a valid signal indication from valid signal detector 136, an indication from an output of wait to add average circuit 156 that the delay established by this circuit is over, and a valid test cycle signal output from a valid test cycle discriminator 158 (explained below), the ETI output enters the averaging circuit 154. The ETI output is then averaged by the averaging circuit with previously received ETI outputs for the veneer sheet to produce an average signal representing the average travel time for ultrasonic signals to pass between the rolling transducers.

As the veneer leaves the test zone, a material sensor 160, comprising the photosensors 30, transmit a signal to a state sequencer 162. Thereupon the state sequencer produces an output to a grade determination circuit 164 which causes this latter circuit to compare an input of the average signal from the averaging circuit with averages assigned to various grades of veneer. The results of this comparison are sent by the grade determination circuit to the sheet marking apparatus 24 to cause the marking of an appropriate grade on the veneer.

A poor data detector 166 monitors averaging circuit 154 and transmits an overload signal to valid test cycle discriminator 158 whenever the averaging circuit has received its capacity of average signals for a particular sheet. This overload signal causes valid test cycle discriminator 158 to block the further entry of new data into the averaging circuit so that the grade for the sheet is determined from the information stored prior to the overload condition. The poor data detector also sends a signal to an input of the grade determination circuit whenever not enough measurements were taken for a sheet to provide a reliable grade indication. When this occurs, the sheet is marked with a reject grade and poor data is indicated.

When a sheet leaves the test zone, state sequencer 162 also produces an output to averaging circuit 154 which resets this circuit in preparation for the next sheet of veneer. In addition, an output from the state sequencer is also sent to the poor data detector to indicate that a particular sheet has left the test zone. Also, a read signal from the state sequencer is fed to a digital voltmeter 168 causing the voltmeter to read the output of the averaging circuit when a sheet leaves the test zone.

The circuit also includes a calibration signal generator 170 having an output coupled through switch 130 to the signal threshold detector when calibration of the circuit is desired. During calibration, the output of receiver 18 is blocked from signal threshold detector 132 by switch 130. In addition, a signal is fed through switch 130 to state sequencer 162 and overrides the output of material sensor 160 so that the state sequencer operates as if a sheet is in the test zone. Calibration signal generator 170 produces a signal of known and adjustable time length. This enables calibration of the circuit as one grade threshold can be established to correspond to a signal of one time length from the signal generator, another to a signal of a different length, and so on.

TRANSMITTER

A transmitter for causing the generation of ultrasonic signals and the ACO signal is shown in FIG. 7 and is described below.

A one hundred and fifteen volt, sixty hertz, alternating current source is fed through a one amp fuse 172 to a voltage doubler comprised of a pair of 40 microfarad capacitors 174, 176 and a pair of diodes 178, 180. More specifically, the AC voltage is fed to one side of capacitor 174 which has its other side connected to the anode of diode 180 and the cathode of diode 178. The anode of diode 178 is grounded and the cathode of diode 180 is connected to one side of capacitor 178 which has its other side grounded. With this arrangement, a direct current rectified voltage of approximately 325 volts is maintained at the cathode of diode 180 as follows. During negative half cycles of the AC source, capacitor 174 is charged through diode 178. During positive half cycles of the AC source, the capacitor 174 discharges through diodes 180 to thereby charge up capacitor 176. The cathode of diode 180 is also connected through three 4.7 kilohm resistors 182, connected in parallel, to a first side of a 1.0 microfarad capacitor 184.

Capacitor 184 is charged through resistors 182 by capacitor 176. Thus charging occurs during both half cycles of the AC signal and the rectified voltage is doubled.

A silicon controlled rectifier (SCR) 186 is connected between the first side of capacitor 184 and ground so as to cause this capacitor to discharge and in turn cause the generation of an ultrasonic signal as explained below. The other side of capacitor 184 is connected by the coaxial cable 76 through shaft 46 to the relative positive side of the primary winding 188 of the transformer 74 inside rolling transducer 10. The other side of primary winding 188 is grounded. The secondary winding 190 of the transformer is connected across transducer assembly 56 with its relative positive side of the winding grounded. Thus, windings 188, 190 are of opposite relative polarities as indicated by polarity dots 192.

When SCR 186 fires, in response to a triggering pulse on a line 194 which is generated as explained below, capacitor 184 discharges through the loop formed by the conducting SCR and primary winding 188. During discharge, the lower portion of primary winding 188 in FIG. 7 is positive so that a positive pulse is applied from the upper portion of secondary winding 190 to transducer 56. This positive going pulse is of high voltage, on the order of 5 kilovolts, and is represented by a wave form 196. In response to this pulse, transducer 56 generates an ultrasonic signal which is then introduced into the veneer sheet 14. As capacitor 184 discharges, current eventually reverses direction because of resonance effects in the transformer-transducer circuit and provides a back voltage that turns off the SCR. SCR 186 remains off while capacitor 184 fully charges, and is then fired again.

The AC source is also connected through a 100 kilohm resistor 198 to the base of an ACO signal generating NPN transistor 200 having a grounded emitter. A diode 202 has its anode grounded and its cathode connected to the base of transistor 200 so that, during negative half cycles of the ac source, diode 202 conducts and maintains the voltage at the base of transistor 200 at approximately ground. A five volt dc biasing voltage is supplied through a 4.7 kilohm resistor 204 to the collector of transistor 200. A negative going ACO synchronizing signal, of a duration equal to the duration of one half cycle of the ac source, is taken from the collector of transistor 200 on a line 22. that is, when the ac voltage is negative, transistor 200 is off, no current flows through resistor 204 and the collector output is five volts. On the other hand, when the ac voltage is positive, transistor 200 turns on, current flows through resistor 204 and the collector output voltage drops to produce the ACO signal. The synchronous relationship between the ACO signal and ac source is shown by FIGS. 12a and 12b. Although the ACO signal is conveniently generated from the ac source voltage, a synchronizing pulse could be generated internally within the testing circuit.

Triggering of SCR 186 occurs simultaneously with the generation of the negative-going edge of the ACO signal. Thus, the ACO signal provides an indication of when an ultrasonic signal is generated for transmission into the veneer.

In the SCR triggering portion of the transmitter circuit, the ac source is fed through a 100 kilohm resistor 206 to the base of an NPN transistor 208 which has its emitter grounded. A diode 210 has its anode grounded and its cathode connected to the base of transistor 208. This diode operates like diode 202 to prevent the voltage at the base of transistor 208 from dropping below ground during negative half cycles of the ac source. The collector of transistor 208 is connected to the base of another NPN transistor 212 and is also connected through a 10 kilohm resistor 214 to a five volt dc supply. The collector of this transistor 212 is connected to the base of an NPN transistor 216, is connected through a 51 kilohm resistor 218 to ground, and is also connected through an 8.2 kilohm resistor 220 to a 5 volt dc supply. The emitter of transistor 212 is connected to the emitter of transistor 216, is connected through a 220 ohm resistor 222 to ground and is coupled through a 0.22 microfarad capacitor 224 to line 194 and thus to SCR 186. The line 194 side of capacitor 224 is connected through a 56 ohm resistor 226 to ground to provide wave-shaping of the triggering voltage supplied to the SCR. Also, transistor 216 has its collector connected to one side of a 4.7 kilohm resistor 228 which has its other side connected to a 5 volt dc supply. The collector of transistor 216 is also coupled through a 0.15 microfarad capacitor 230 to ground.

During the positive going portions of the ac source voltage, transistor 208 turns on so that the base of transistor 212 is effectively grounded. As a result, no base driving current is provided to this latter transistor and it is off. This in turn causes the voltage at the collector of transistor 212, and hence at the base of transistor 216, to rise. Consequently, transistor 216 turns on so that additional current flows through resistor 222 to ground. As a result, the voltage at the emitter of transistor 216 rises and charges capacitor 224 so that a positive voltage triggering signal is fed on line 194 to the silicon controlled rectifier.

In this manner, SCR 186 fires and causes the generation of an ultrasonic signal with each positive going zero crossing of the ac source. At the same time, the synchronization signal ACO is generated.

RECEIVER

Upon the detection of ultrasonic signals within the veneer, rolling transducer 16 transmits electrical signals corresponding to these detected signals to receiver 18 (FIG. 7) which is housed within a radio frequency shielded box. The main function of receiver 18 is to filter and amplify the output of rolling transducer 16 for use by the testing circuit.

The rolling transducer output is coupled through a 120 picofarad capacitor 232 to the noninverting input of an operational amplifier 234. This noninverting input is grounded through a 100 kilohm resistor 235. An 8.2 kilohm feedback resistor 236 has one side connected to the output of amplifier 234 and its other side connected to the inverting input of amplifier 234 and also grounded through a 1.0 kilohm resistor 238. A 2.7 kilohm resistor 240 connected between the rolling transducer side of capacitor 232 and ground cooperates with this capacitor to filter out some of the low frequency noise from the conveyor. The output of amplifier 234 is coupled through a 0.2 microfarad capacitor 242 and a 470 ohm resistor 244, connected in series, to the inverting input of an amplifier 246. The noninverting input of this amplifier is grounded. A low pass feedback network comprising a 4.5 picofarad capacitor 248 in parallel with a 10 kilohm resistor 250 is connected between the inverting input and the output of amplifier 246. The output of amplifier 246 is fed to the noninverting input of an amplifier 252 wherein it is amplified and transmitted on a line 254 through test switch 130 (FIG. 8) to an input of signal threshold detector 132. The output of amplifier 252 is also fed back to its inverting input.

When connected as described above, receiver 18 produces a voltage output on line 254 of a magnitude representing the magnitude of the signal detected by the rolling transducer 16. These detected signals could arise from extraneous sources, such as the conveyor, in addition to signals tranvelling from transmitter rolling transducer 10.

SIGNAL THRESHOLD DETECTOR

Figure 8:
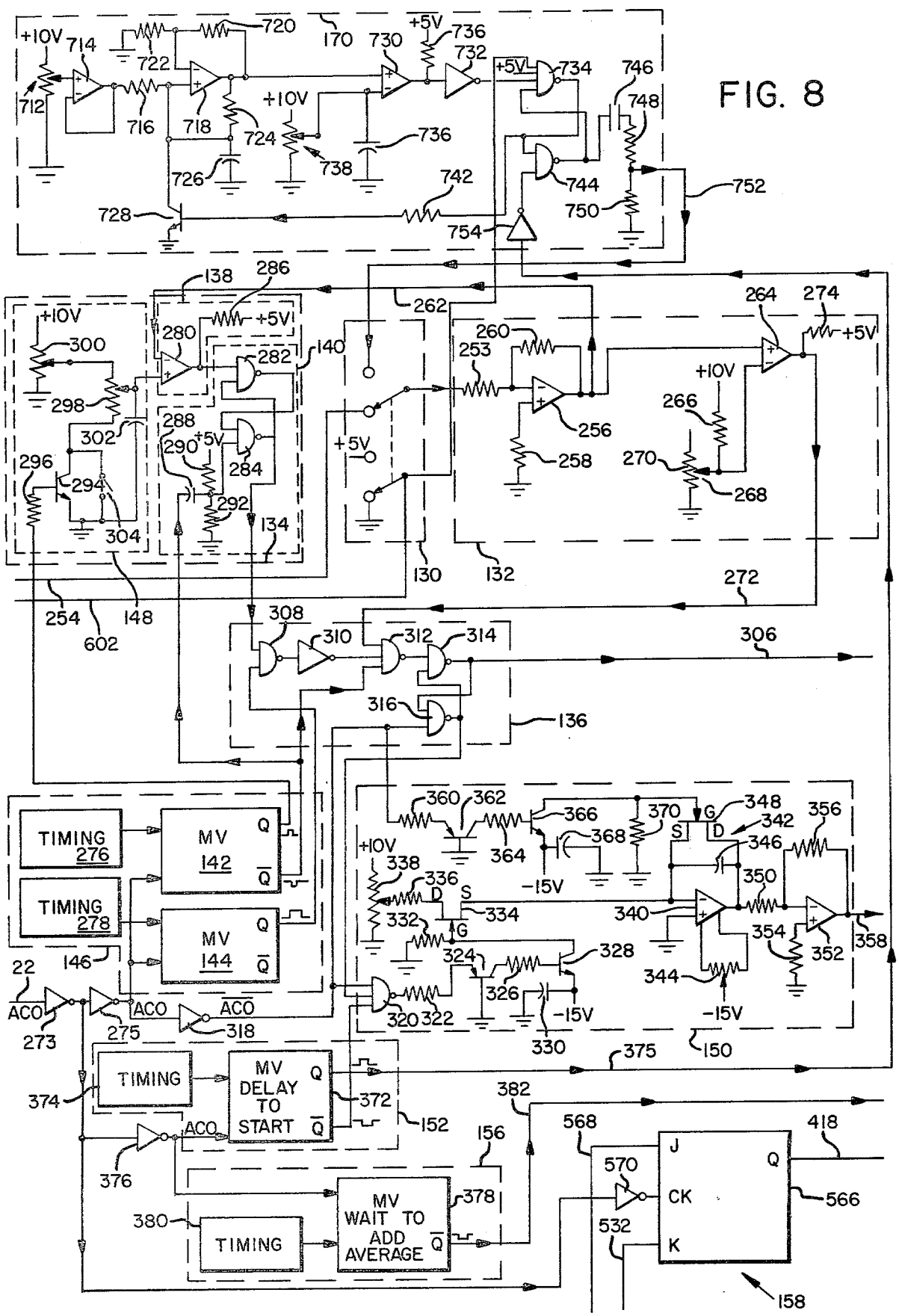
FIG. 8 is an electrical schematic diagram of the signal threshold detector noise discriminator, time window, and other circuitry of FIG. 6.

Referring to FIG. 8, signals from the output of receiver 18 on line 254 pass through a normally closed contact of switch 130 to signal threshold detector 132. Detector 132 compares the voltage level of the receiver output with a reference voltage. In addition, detector 132 sends a signal received indication to valid signal detector 136 at the time when the amplitude of the output voltage exceeds the amplitude of the reference voltage. The normally closed contact of switch 130 is connected through a 10 kilohm resistor 253 to the inverting input of an amplifier 256 of a signal inversion and amplifier gain stage. The noninverting input of amplifier 256 is grounded through a 4.7 kilohm resistor 258 and a 20 kilohm feedback resistor 260 is provided between the output and inverting input of amplifier 256. The purpose of inverting the receiver output in amplifier 256 is to enable the threshold detector to detect the first tension wave of a travelling ultrasonic signal rather than the first compression wave. As this tension wave has a greater amplitude than the compression wave, a more reliable threshold crossing time is detected and an increased noise margin results. Threshold crossing time refers to the time that the amplitude of the detected signal, as amplified by amplifier 256, exceeds the reference voltage of detector 264.

The output of amplifier 256 is fed on a line 262 to noise discriminator 134 and to the noninverting input of a voltage comparator 264. A reference voltage is supplied to the inverting input of the comparator. The comparator operates to produce a high logic level output, a one, whenever the amplitude of the reference voltage is exceeded by the amplitude of the receiver output from amplifier 256. Otherwise, comparator 264 produces a low logic level, a zero, output. The reference voltage is set at a level corresponding to a minimum receiver outut level expected when rolling transducer 16 detects a travelling ultrasonic signal. Only detected signals of a magnitude exceeding the reference level cause a high logic level signal, a valid signal indication, to be sent to valid signal detector 136.

The reference voltage is adjustable so that it may be varied to suit a particular application. For example, it can be increased when signals travel through a shorter length of material and less attenuation is expected. The inverting input of comparator 264 is connected through a 1 kilohm resistor 266 to a 10 volt dc supply. In addition, this input is connected to a wiper arm 268 of a 100-ohm potentiometer 270. Varying the position of the wiper arm adjusts the reference voltage in a conventional manner.

The output of comparator 264 is fed on a line 272 to an input of valid signal detector 136 which, in its illustrated form, comprises a plurality of gates operable as explained below. In addition, the comparator output is connected through a 4.7 kilohm resistor 274 to a 5 volt dc supply so that the high and low values of the comparator output are at logic levels suitable for operating the gates within the valid signal detector.

TIME WINDOW CIRCUIT

Time window circuit 146 (FIG. 8) is set to provide a minimum expected travel time for ultrasonic signals to travel through the veneer from the transmitter. That is, signals detected after transmission of an ultrasonic signal by the transmitter and before this minimum time has elapsed are disregarded. Furthermore, the time window circuit is set to provide a maximum expected time of travel so that signals detected after this maximum time is over are also disregarded.

The ACO signal on line 206 is fed through a pair of logic inverters 273, 275 and then to triggering inputs to range gates 142, 144. These logic inverters increase the drive capability of the ACO signal. Each of the range gates 142, 144 comprises a conventional one-shot multivibrator with respective conventional resistor-capacitive timing circuits 276, 278. When triggered by the negative going edge of the ACO signal, range gate 142 produces a positive going square pulse at its Q output to the variable noise level circuit 148 for purposes explained below. At the same time, the $\overline{Q}$ output of this range gate goes negative and is fed to valid signal detector 136 and the noise threshold latch 140 for reasons subsequently explained. The duration of the range gate 142 signal can be adjusted by timing circuit 276 and is established to end shortly before the minimum expected travel time of ultrasonic signals through the sheet material. For example, when sheets of veneer are being tested with the rolling transducers spaced ninety-three inches apart, the duration of range gate 142 output is set at approximately 300 microseconds and is represented in FIG. 12c. This is below the expected minimum time of around 350 microseconds for an ultrasonic signal to travel in the veneer between the rolling transducers. The Q output of range gate 144 also goes positive upon receipt of the ACO signal and is fed to valid signal detector 136. The duration of this output can be adjusted by timing circuit 278 and is established to be longer than the maximum expected travel time of an ultrasonic signal between the transducers. In the above example, with the range gate 142 output set to last 300 microseconds, the range gate 144 output is typically set to last 1100 microseconds, as represented in FIG. 12d.

With these settings, a time window of 800 microseconds is established. As shown in FIG. 12e, this time window begins 300 microseconds after the ACO signal at the end of the range gate 142 output, and ends 1100 microseconds after the ACO signal (at the end of the range gate 144 output). Signals received by valid signal detector 136 from threshold detector 132 that are not within the established time window are disregarded as being invalid in a manner described below.

NOISE DISCRIMINATOR

As previously mentioned, noise discriminator 134 determines whether or not a detected signal has arisen from a travelling ultrasonic signal transmitted by rolling transducer 10, or from extraneous noise, such as from the conveyor. To accomplish this, the noise discriminator is set at a maximum level of the amplitude of receiver 18 output signals expected from detected transmitted ultrasonic signals. Detected signals of a level greater than this maximum are disregarded as originating from noise.

Looking at FIG. 8, the output of amplifier 256 is fed on line 262 to the inverting input of a voltage comparator 280 of noise detector 138. The noninverting input of the voltage comparator constitutes a noise reference voltage and is obtained from a variable noise level circuit 148. Whenever the magnitude of the voltage on line 262 is below the noise reference voltage, comparator 280 produces a logic one output to the noise threshold latch 140. Latch 140 is comprised of a pair of NAND gates 282, 284 which are cross connected with the output of each fed to an input of the other. The comparator 280 output is also connected through a 4.7 kilohm resistor 286 to a five volt dc supply so that the output of comparator 280 is at logic levels compatible with the logic levels required by NAND gate 282.

Noise threshold latch 140 also includes a reset circuit triggered by the falling edge of the $\overline{Q}$ output of range gate 142. This falling edge resets the latch to its initial state prior to the generation of each ultrasonic signal. In its initial state, the output of gate 282 is at a logic zero level and of gate 284 is at a logic one level. To accomplish resetting, the $\overline{Q}$ output of range gate 142 is coupled by a 0.1 microfarad capacitor 288 to the reset input of gate 284. In addition, this reset input is connected through a 10 kilohm resistor 290 to a five volt dc supply and is grounded through another 10 kilohm resistor 292. With this connection, the reset input of gate 284 is maintained at a logic one level until the $\overline{Q}$ output of range gate 142 goes to logic zero level upon the occurrence of the ACO signal. When each ACO signal occurs, the reset input of gate 284 momentarily goes to a logic zero, due to capacitor 288, and resets noise threshold latch 140 to its initial state.

As long as the magnitude of the detected signal does not exceed the noise reference voltage, the noise threshold latch remains in its initial state and a logic one signal is sent to an input of the valid signal detector 136 from gate 284. On the other hand, when noise is detected, comparator 280 produces a logic zero output which causes the output of gate 282 to go to a logic one and of gate 284 to go to a zero. These gates maintain these outputs, to indicate the detection of noise to valid signal detector 136 until the noise threshold latch 140 is reset at the next ACO signal.

The variable noise level circuit 148 adjusts the noise reference voltage as a function of time from the falling edge of the ACO signal, and hence from the generation of an ultrasonic signal. In the illustrated form, the noise reference voltage is maintained at a low level between the negative-going edge of the ACO signal and the end of the range gate 142 output. Thereafter, the noise level is raised. As a result, the circuit is relatively more sensitive to noise occurring prior to the end of the expected minimun travel time for transmitted ultrasonic signals. Yet, the level rises during times that transmitted ultrasonic signals are expected to reach receiver 18 so that these signals will not be considered to be noise.

The variable noise level circuit includes an NPN transistor switch 294 having its base connected through a 1 kilohm resistor 296 to the Q output of range gate 142 and its emitter grounded. The collector of this transistor is connected through the wiper arm of a potentiometer 298 to the noninverting input of comparator 280. Potentiometer 298 is connected to the wiper arm of another potentiometer 300 which is supplied by a 10 volt dc source. A 0.1 microfarad capacitor 302 couples the noninverting input of comparator 280 to ground. In addition, a switch 304 is connected between the collector of transistor 294 and ground.

When the range gate 142 Q output is low, transistor 294 is off. Consequently, the noise reference voltage at the noninverting input of comparator 280 is set by the position of the wiper arm of potentiometer 300 as no current flows through potentiometer 298. This level is adjustable up to the maximum voltage supplied to the potentiometer. In contrast, at the start of the ACO signal, the Q output of range gate 142 goes positive so that transistor 294 turns on. As a result, current flows through potentiometer 298 to ground and causes the noise reference voltage to drop. The magnitude of this reference voltage is established by the position of the wiper arms of potentiometers 298, 300 and can be measured when switch 304 is closed to short transistor 294.

This change in noise reference voltage from the high to low levels and back is not instantaneous, but is delayed by the RC time constant set by capacitor 302 and the resistors of the variable noise level circuit. By delaying the change, noise of a greater magnitude than the low noise level setting is permitted at the time of the ACO signal without triggering the noise threshold latch. Similarly, spurious noise pulses occurring at the end of the range gate 142 signal will still trigger the noise hit latch because the noise reference voltage has not yet risen to its high value.

VALID SIGNAL DETECTOR

Valid signal detector 136 comprises a gating circuit which produces a logic level one output on a line 306 to averaging circuit 154 whenever a valid signal has been detected. The term valid signal means those signals which exceed the minimum level established by signal threshold detector 132, have occurred prior to the detection of noise by noise discriminator circuit 134, and which occur within the time window established by time window circuit 146.

Valid signal detector 136 includes a NAND gate 308 which receives one input from gate 284 of noise threshold latch 140 and has its other input connected to the Q output of range gate 144. The output of gate 308 is fed through an inverter 310 to an input of a three input NAND gate 312. The other inputs of NAND gate 312 are connected respectively to the $\overline{Q}$ output of range gate 142 and by line 272 to the output of signal threshold detector 132. The output of gate 312 is fed to an input of another NAND gate 314 which has its output connected to an input of NAND gate 316 and also to line 306 leading to the averaging circuit. The output of gate 316 is fed back to an input of gate 314 so that these gates are cross connected and form a valid signal detector latch. Resetting of this latch is accomplished at the end of the AC0 signal by the falling edge of the inverted AC0 signal from an inverter 318 fed to an input of gate 316. To obtain the inverted ACO signal, inverter 318 inverts the output of inverter 275. At the end of each ACO signal, the gate 314 output is reset to its initial state of a zero logic level and the gate 316 output is reset to an initial logic level one. Upon detection of a valid signal, the output of gate 314 goes to a one and the output of gate 316 goes to a zero. These gates remain in this state until they are again reset.

Assuming that a valid signal is detected, both inputs to gate 308 are at the logic one level so that its output is zero and the output of inverter 310 is a one. In addition to the logic one from inverter 310, gate 312 receives a logic one on line 272 from signal threshold detector 132 and a one from the $\overline{Q}$ output of range gate 142. Consequently, gate 312 produces a zero input to gate 314 so that this gate produces a one output on line 306 indicating a valid signal. When the gate 314 output goes to one, the gate 316 output goes zero and gates 314, 316 are latched until they are again reset.

Next assume that noise has been detected by noise discriminator circuit 134. In such a case, the input to gate 308 from noise threshold latch 140 is zero so that the output of this gate is a one. As a result, the output of inverter 310 is a zero and of gate 312 is a one. Furthermore, the output of gate 314 remains a zero due to the one input from gate 312 so that a valid signal is not indicated on line 306. After noise is detected, the zero output of valid signal detector 136 is fixed until after the next ACO signal. This occurs because the output of noise threshold latch 140 is fixed at zero until the next ACO signal.

Also, except between the negative-going edge of the ACO signal and the end of the positive signal from the Q output of range gate 144, the gate 308 output is fixed at one because of the zero from range gate 144. Consequently, detector 136 can't indicate a valid signal to the averaging circuit except when the Q output of range gate 144 is a one. In other words, the only time a one input from inverter 310 appears at gate 312 is when there hasn't been any noise detected and during the time between the ACO signal and the end of this range gate 144 output.

In addition, until a logic one level appears on line 272 from the threshold detector, the output of gate 312 is a logic one and a valid signal is not indicated. Also, for the duration of the negative $\overline{Q}$ signal from range gate 142, the output of gate 312 is a one and a valid signal is not indicated.

In this manner, a logic one level appears on line 306 to indicate a valid signal at the first time that a signal exceeding the threshold of threshold detector 132 occurs, which is in the time window, and as long as noise has not been detected between the ACO signal and the occurrence of this signal.

TIMER

The timer for timing the travel times of ultrasonic signals shown in FIG. 8 comprises an elapsed time integrator 150 which produces a voltage of a magnitude representing the travel time. In general, ultrasonic signals travel faster through higher quality veneer and cause the elapsed time integrator to produce voltages lower in magnitude than produced for lower quality veneer where travel times are longer.

Elapsed time integrator 150 comprises a ramp generator which produces an output voltage that increases at the rate of 1 volt per 100 microseconds. This ramp voltage starts at zero, after the end of a time delay from the ACO signal, which is set by delay to start ETI circuit 152, and increases until such time as a valid signal is detected. Thereafter, the ramp generator output voltage remains at the level reached when detection of the valid signal occurred. Subsequently, the ramp generator output, which is the output of elasped time integrator 150, is fed to averaging circuit 154 FIG. 10 and the ramp generator output is reset to zero in preparation for the next ACO signal.

Elapsed time integrator 150 comprises a NAND gate 320 connected through a 3.9 kilohm resister 322 to the emitter of a PNP transistor 324. The base of transistor 324 is grounded and its collector is connected through an 8.2 kilohm resistor 326 to the base of an NPN transistor 328. The emitter of this latter transistor is connected to a negative fifteen volt dc supply which is filtered by a 0.1 microfarad capacitor 330 connected between the emitter and ground. The collector of transistor 328 is grounded through a 10 kilohm resistor 332 and is also connected to the gate of a field effect transistor 334. FET 334 operates as an analog switch under the control of NAND gate 320 and the transistors 324, 328.

The drain of FET 334 is connected through a 1 megohm resistor 336 to the wiper arm of a potentiometer 338 supplied by a 10 volt dc supply. The source of transistor 334 is connected to the inverting input of an amplifier 340 which is included in a ramp generator integrator circuit indicated generally as 342. The noninverting input of amplifier 340 is grounded and a balancing potentiometer 344 is provided for adjusting the amplifier so that when its input is zero its output is also zero. A 0.001 microfarad integrating capacitor 346 is connected between the inverting input of amplifier 340 and its output.

The output of integrator 342 is fed through a 10 kilohm resistor 350 to the inverting input of an amplifier 352. The noninverting input of amplifier 352 is grounded through a 4.99 kilohm resistor 354 and a feedback resistor 356 is connected between the output and a inverting input of the amplifier. The output of amplifier 352, which is the inverted output of integrator 342, is fed on a line 358 to averaging circuit 154 wherein it is used for veneer grading purposes as explained below.

A field effect transistor switch 348 is connected in parallel with capacitor 346 to conduct and provide a discharge path for the capacitor shortly after the end of each ACO signal. This allows capacitor 346, and hence integrator 342 to initialize to a zero output prior to the occurrence of the next ACO signal. To control the operation of FET switch 348, the ACO output of inverter 318 is fed through a 3.9 kilohm resistor 360 to the emitter of a PNP transistor 362 having a grounded base. The collector of transistor 362 is connected through an 8.2 kilohm resistor 364 to the base of an NPN transistor 366. The emitter of transistor 366 is connected to a negative fifteen volt dc supply which is filtered by a 0.1 microfarad capacitor 368 connected between the emitter and ground. The collector of transistor 366 is connected through a 10 kilohm resistor 370 to ground and is also connected to the gate of FET switch 348.

At the end of each ACO signal, the voltage at the emitter of transistor 362 goes negative and the transistor turns off. Consequently, no base current is supplied to transistor 366 and this latter transistor also turns off. As a result, the voltage at the gate of switch 348 rises to ground potential through resistor 370 so that switch 348 conducts and capacitor 346 discharges. On the other hand, at the start of each ACO signal, the voltage at the emitter of transistor 362 goes positive and the transistor turns on. At the same time, transistor 366 also turns on. With transistor 366 on, the voltage at its collector drops toward negative fifteen volts and causes switch 348 to turn off so that it no longer discharges capacitor 346. In this manner, integrator 342 is reset to begin producing a ramp voltage output at each ACO signal.

Returning to gate 320, when the output of this gate is zero, transistors 324 and 328 are off. Consequently, the voltage at the gate of FET switch 334 is at ground potential and this FET is on. When FET switch 334 is on, and assuming switch 348 is off, the constant voltage from potentiometer 338 is integrated by capacitor 346 to produce a ramp voltage at the output of integrator 342. As long as the gate 320 output remains zero, integration continues until the end of the ACO signal when capacitor 346 is discharged.

In contrast, when the output of gate 320 goes to a logic one, transistors 324 and 328 both turn on and the voltage at the gate of FET switch 334 drops. This in turn causes FEt 334 to turn off so that integration by capacitor 346 stops. Thereafter, capacitor 346 holds its charge, and hence the output voltage of integrator 342 is held at the level reached when the switch 334 is turned off.

The output of gate 320 is positive, thereby preventing integration by integrator 342 for a time from each ACO signal until the end of a delay time set by delay to start circuit 152. That is, at each ACO signal, the $\overline{Q}$ output of a one-shot multivibrator 372 goes to zero and is fed to an input of gate 320 thereby causing output of this gate to go to a one and preventing integration. At the end of this delay time, the $\overline{Q}$ output of multivibrator 372 goes positive. Consequently, depending upon the level of its other inputs, the gate 320 output can then go to zero and integration can begin. The multivibrator 372 is triggered by the falling edge of the ACO signal received from the output of an inverter 376 fed from inverter 273. In addition, its Q output is fed on a line 375 to a triggering input of calibration signal generator 170.

A conventional timing circuit 374, comprised of resistor and a capacitor, establishes the delay time of multivibrator 372. This delay time is adjustable and is set to compensate for time taken by ultrasonic signals to pass from transducer 56 of rolling transmitter transducer 10 to the sheet material and from the sheet to the transducer of rolling receiver transducer 16. Consequently, the travel time voltage representations obtained from integrator 342 represents time actually spent by a signal in the veneer after subtracting out time spent in the rolling transducers. Although this feature is optional, it facilitates use of the apparatus as travel times obtained by the apparatus can be compared directly with laboratory measurements of travel times taken without the use of rolling transducers. For example, laboratory measurements can be taken and used to assign average travel times for particular grades of veneer. The apparatus can then be directly set up to mark grades corresponding to these known average travel times without having to compensate for the effect of the rolling transducers of these travel times. As a more specific example, the delay time is normally set at about 40 microseconds which is approximately equal to the expected travel time of the signals through both transducer wheel assemblies.

The ACO output of inverter 318 is also fed to an input of NAND gate 320. Thus, at the end of the ACO signal, this input to gate 320 goes zero so that the gate 320 output goes to one to in turn block integration. Also, during each ACO pulse, the output of inverter 318 is a one so that the gate 320 can be either a one or a zero depending upon the level of its other inputs.

The remaining input to gate 320 is taken from the output of gate 316 and goes zero only if a valid signal has been detected by signal detector 136. Therefore, during each ACO signal and after the delay established by delay to start circuit 152 is over, the gate 320 output only goes zero if a valid signal is detected. Thus, integration by integrator 342 continues until such time as a valid signal is detected. For example, looking at the first waveform in FIGS. 12 g and h, this waveform represents a relatively fast travel time. Thus, the ETI output increases until the valid signal is received and then holds the level reached at this time until the circuit discharges at the end of the ACO signal. During the next ACO signal, represented by the second waveform in FIGS. 12 g and h, no valid signal is received and the ETI 150 output increases along a ramp until the end of the ACO signal. Finally, during the next ACO signal, the third waveform in these figures, a valid signal is received later in time from the ACO signal than in the first waveform. Thus, ETI 150 output reaches a higher level, representing a slower travel time and a lower quality indication, before integration ends upon receipt of the valid signal.

WAIT TO ADD AVERAGE CIRCUIT

Wait to add average circuit 156, delays the entry of the output of integrator 342 into the averaging circuit 154 so that the elapsed time integrator integrates over a constant length of time for each valid signal. Because averaging circuit 154 averages each of the valid signals received from the elapsed time integrator, integrators 384, 386 must integrate over uniform time periods for each valid signal. Otherwise, the valid signals would not be weighted equally when they are averaged.

Wait to add average circuit 156 comprises a one-shot multivibrator 378 which is triggered at the start of the ACO signal to produce a negative going pulse at its $\overline{Q}$ output. The duration of this negative going pulse is established by a conventional timing circuit 380. This duration is set to be longer than the travel time expected for any valid signals so that each of the valid signals will be received before the average circuit 154 is updated with new information. For the wood veneer testing application under discussion, a delay to add to average of 1200 microseconds is suitable. The $\overline{Q}$ output of multivibrator 378 is fed on a line 382 to the averaging circuit 154 for blocking the entry of new information into the averaging circuit until after the $\overline{Q}$ output goes high.

AVERAGING CIRCUIT

Figure 10:
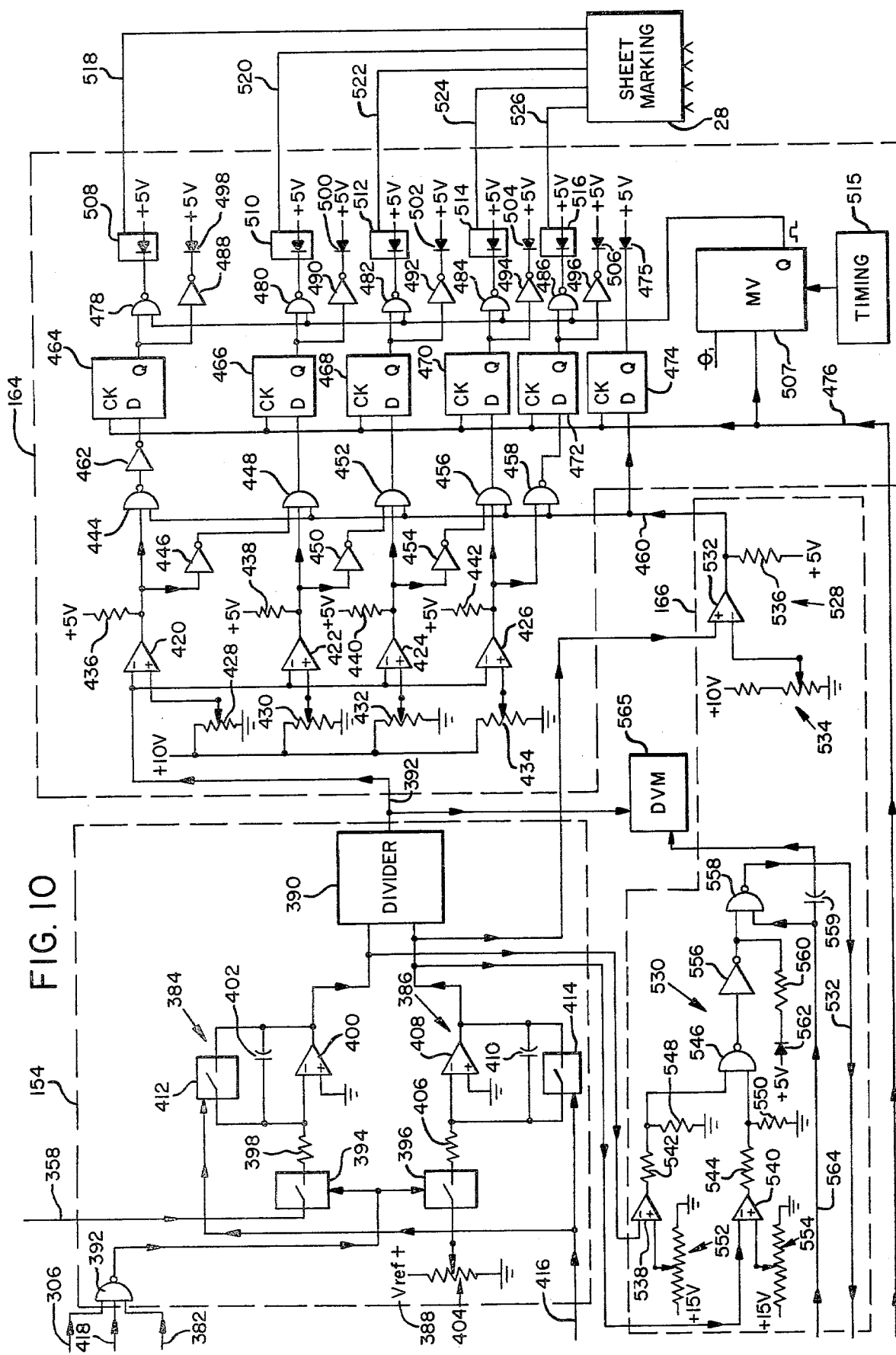
FIG. 10 is an electrical schematic diagram of the averaging, grade determination and poor data detector circuits of FIG. 6.

Averaging circuit 154, FIG. 10, includes a valid signal integrating portion 384 and a reference voltage integrating portion 386. Integrator portion 384 operates in a known manner to integrate the signal representing each valid signal which appears on line 358 from ETI 150. In this manner, each new valid signal is added to previously integrated voltage levels representing previously detected valid signals. Simultaneously with the addition of the new information into signal integrating portion 384, reference integrator portion 386 integrates a voltage from a voltage reference source 388 for the same amount of time. A divider circuit 390 divides the voltage from signal integrator 384 by the voltage from reference integrator 386 to produce an averaging circuit output on a line 392. The averaging circuit output represents the average value of the valid signals received from the elapsed time integrator and hence represents an average of travel times for ultrasonic signals to pass through the veneer sheet.

Averaging circuit 154 includes a three input NAND gate 392 having its output connected to a pair of voltage controlled switches 394, 396 of the respective integrator portions 384, 386. Whenever the inputs to gate 392 are all ones, the output of this gate goes to zero and switches 394, 396 simultaneously turn on. When switch 394 is on, the output of the elapsed time integrator 150 is fed on line 358 through an input resistor 398 to the inverting input of an amplifier 400 having a grounded noninverting input. An integrating capacitor 402 is connected between the output of amplifier 400 and its inverting input forming a conventional voltage integrator. Thus, when switch 394 is on, the signal from elapsed time integrator 150 charges capacitor 402. The output of amplifier 400 is fed to the numerator input of a commercially available divider 390. One suitable divider is a programmable multifunction module, model number 433, produced by ANALOG DEVICES Company, Route 1, Industrial Park, Norwood, Massachusetts.

Similarly, when switch 396 is on, the reference voltage set by the position of a wiper arm of a potentiometer 404 is fed through an input resistor 406 to the inverting input of an amplifier 408 of integrating portion 386. The noninverting input of amplifier 408 is grounded and an integrating capacitor 410 is connected between the output of amplifier 408 and its inverting input. Thus, during times that switch 396 is closed, the reference voltage is integrated by capacitor 410. The output of amplifier 408 is fed to the denominator input of divider circuit 390.

Both integrating portions 384, 386 include respective voltage switches 412, 414 connected in parallel with respective capacitors 402, 410. These switches are similar in detail to the switching portion of ETI 150 and operate in response to a signal on a line 416 from state sequencer 162 to provide a discharge path for capacitors 402, 410. Discharging of these capacitors occurs after a sheet leaves the test zone and after grade determination circuit 164 has had a chance to utilize the output of divider 390. The circuit for generating the appropriate signal on line 416 is described below in connection with the description of state sequencer 162.

As mentioned above, averaging by averaging circuit 154 only occurs when the output of NAND gate 392 is zero, as otherwise switches 394 and 396 are open. In turn, the output of gate 392 is only zero if its inputs are all ones. These inputs are received on line 306 from the valid signal detector 136 (FIG. 8), on line 382 from the $\overline{Q}$ output of the multivibrator of wait to add average circuit 378, and on a line 418 from the valid test cycle discriminator circuit 158 (FIG. 8). As explained below, discriminator circuit 158 normally produces a one output on line 418 during testing of each sheet of veneer. In addition, wait to add average circuit 378 produces a one output of gate 392 after the end of the zero signal from the $\overline{Q}$ output of multivibrator 378. Also, the signal on line 306 from valid signal detector 136 goes positive with the detection of a valid signal. Therefore, only when a valid signal is detected, the wait to add average delay is over, and valid test cycle discriminator 158 indicates a valid test, is the elapsed time integrator output fed to averaging circuit 154.

Figure 12:
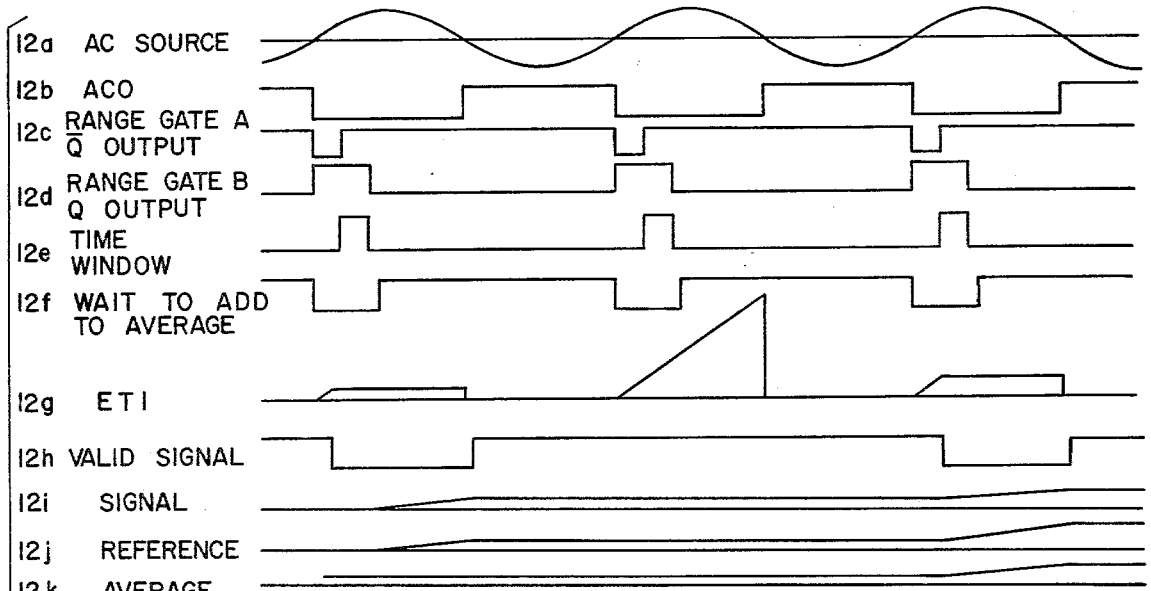
FIG. 12 is a diagram of wave forms generated at various locations within the circuit of FIG. 6.

Referring to FIGS. 12$i$, $j$ and $k$, the operation of the averaging circuit will be described in more detail. After the wait to add to average signal is over, the ETI output shown as the first waveform in FIG. 12$g$ is integrated by integrator portion 384 until the end of the ACO signal. FIG. 12$i$ represents the output of integrator 384 and it is shown to increase. For the same time, the reference integrator 386 integrates the reference voltage and produces an output shown in FIG. 12$j$. The average of these two signals is shown in FIG. 12$k$ and increases only slightly because of the fast travel time represented by this signal. During the second ACO signal, no valid signal is received so that the levels of FIGS. 12$i$, $j$ and $k$ remain the same. During the third ACO signal, the average increases more than during the first ACO signal because a valid signal of a slower travel time was detected. In this manner, an average travel time for the sheet of veneer is obtained.

GRADE DETERMINATION CIRCUIT

The output of averaging circuit 154 is fed to grade determination circuit 164 which compares the voltage level of this output with predetermined voltage levels assigned to particular grades of veneer. From this comparison, the grade of the sheet of veneer is determined.

The divider output on line 392 is transmitted to the inverting inputs of four differential voltage comparators 420, 422, 424, 426. The noninverting inputs of these comparators are connected to respective potentiometers 428, 430, 432, 434 fed by a ten volt dc supply. These potentiometers are adjustable to provide selected voltages representing grade thresholds for different grades of veneer. As a specific example, these voltages may be selected so that whenever the voltage on line 392 represents an average travel time of less than 410 microseconds number one grade veneer will be indicated, between 410-425 microseconds, number two veneer is indicated, between 425-455 microseconds number three veneer is indicated and between 455-460 microseconds number four veneer is indicated. Of course, additional potentiometers could be added in the event more grade thresholds are desired.

The output of each comparator 420,422,424,426 is connected through a respective 1 kilohm resistor 436,438,440,442 to a 5 volt dc supply. As a result, the magnitude of the output of each of these comparators is adjusted to a level compatible with the logic levels required to operate the gating circuits to which these comparators are connected.

The output of comparator 420 is connected to one input of a NAND gate 444 and also through an inverter 446 to an input of an AND gate 448. The output of comparator 422 is connected to an input of an AND gate 448 and through an inverter 450 to an input of an AND gate 452. In addition, the comparator 424 output is connected to an input of an AND gate 452 and through an inverter 454 to an input of another AND gate 456. Also, comparator 426 is connected both to an input of AND gate 456 and to an input of a NAND gate 458. Each of the gates 444, 448, 452, 456, 458 receive an input on a line 460 from poor data detector 166. This input is normally a one unless not enough measurements have been taken for a piece of veneer to reliably determine a grade for the veneer.

The output of gate 444 is fed through an inverter 462 to the D input of a D flip-flop 464. In addition, the outputs of gates 448, 452, 456, 458 are fed to the respective D inputs of D flip-flops 466, 468,470,472. Also, line 460 is connected to the D input of another D flip-flop 474. Flip-flop 474 has its Q output connected to the cathode of a light emitting diode 475 which in turn has its anode connected to a positive five volt dc supply. All light-emitting diodes used in this circuit are constructed with an internal series resistor not shown. The D input of each flip-flop is transferred to its Q output in response to a clocking pulse on a line 476 from state sequencer 162 which is generated when the veneer sheet leaves the test zone. The Q output of each D flip-flop 464, 466, 468, 470, 472 is fed to an input of a respective two input NAND gate 478, 480,482,484, 486. In addition, each of these Q outputs is connected through a respective inverter 488, 490, 492, 494, 496 to the cathode of a respective light emitting diode 498, 500, 502, 504, 506 which in turn has its anode connected to a 5 volt dc supply. The other input of each NAND gate 478, 480, 482, 484, 486 is coupled to the Q output of a multivibrator 507.

The outputs of these NAND gates are each connected to the cathode of a respective light emitting diode 508,510,512,514,516 which have their anodes connected to a five volt dc supply. These latter diodes are optically coupled, on respective lines 518,520,522,524,526 in a conventional manner to relays in sheet marking and tally count circuit 24 so that the respective relay is operated when its associated diode conducts. These relays in turn each control a separate spray head and electromechanical impulse counter, not shown, which may spray a specified grade indicating color of ink on the veneer and increment a counter when the associated diode conducts. The duration of spraying is determined by the duration of the Q output of multivibrator 507 and is established by a conventional timing circuit 515. Typically the spray time is set at forty to one hundred milleseconds. Multivibrator 507 is triggered by the clocking pulse on line 476 from the state sequencer.

The grade determination circuit operates as follows with number one grade veneer, of high quality, being controlled by the setting of potentiometer 428, number two grade controlled by potentionmeter 430, number three by potentiometer 432 and number four by potentiometer 434.

When number one grade veneer is tested, the output of comparator 420 is a logic one. Assuming poor data is not indicated on line 460, then both inputs to gate 444 are logic one so that its output is a logic zero. This output is inverted by inverter 462 to appear as a logic one at the D input of flip-flop 464. When a clocking signal appears on line 476, as the sheet leaves the test zone, the one at the D input is transferred to the Q output and results in a zero at the output of inverter 488. When this occurs, diode 498 is forward biased and lights up to give a visual indication of the grade. In addition, upon the occurrence of the pulse from multivibrator 507, both inputs to gate 478 are logic one so that this gate produces a logic zero output. Consequently, diode 508 is forward biased and turns on. As a result, a signal is sent on line 518 to the number one grade sprayhead of the sheet marking circuit and the sheet is marked.

When number one veneer is tested, a zero is maintained at the D input to the other flip-flops 466,468,470,472 so that only the number one grade sprayhead is activated. That is, the outputs of comparators 422 through 426 are all ones and of inverters 446 through 454 are zeros. Thus, the outputs of gates 448 through 458 and hence at the D input of these other flip-flops are zero.

On the other hand, assuming the voltage is higher than the level of potentiometer 428, but lower than the level of potentiometer 430. In this case, the output of comparator 420 is zero, of gate 444 is a one, and of inverter 462 is a zero, so that the number one grade sprayhead is disabled. In addition, the output of inverter 446 and comparator 422 are ones so that a one is applied from gate 448 to flip-flop 466. Therefore, the number two grade sprayhead will be activated in the manner explained above for the number one sprayhead. At the same time, the output of AND gate 452 is zero because of a zero input from inverter 450 so that the number three sprayhead is disabled. Also, the output of AND gate 456 is zero, and the number four sprayhead is disabled, because of the zero input to this gate from inverter 454.

In a similar manner, voltages between the levels established by potentiometers 430 and 432 activate the number three sprayhead and those between the levels established by potentiometers 432 and 434 activate the number four sprayhead. Furthermore, voltages higher than the level of potentiometer 434 indicates reject grade, and in this implementation, no spraying occurs.

In this manner, the grade indication on a particular sheet of veneer depends upon the average voltage level indicated by the divider 390 and hence upon the average travel time of ultrasonic signals transmitted through the sheet.

If during testing of a sheet, poor data detector circuit 166 determines that insufficient time measurements have been taken to accurately grade the sheet, then a zero output is produced, as explained below, on line 460. When this happens, the Q output of each flip-flop 464,466,468,472 is zero so that the sprayheads are not activated.

To differentiate between poor data and reject grade, LED diode 475 only turns on when insufficient measurements have been taken, due to the zero output from flip-flop 474 at such times. In contrast, this diode doesn't light up if the veneer is of reject grade because flip-flop 474 has a positive Q output.

POOR DATA DETECTOR

Poor data detector 166 includes an insufficient data sample indicator portion 528 for indicating that not enough travel time measurements have been averaged by divider 390 during testing of a sheet to provide a meaningful sheet grade indication. The poor data indicator also includes an overload indicating portion 530 for providing a signal on a line 532 to valid test cycle discriminator 158 (FIG. 8) whenever the numerator or denominator inputs of divider 390 have reached their maximum allowable voltage inputs. This latter signal causes the valid test cycle discriminator to block the entry of additional travel time measurements for the sheet into the averaging circuit. This prevents distortion of information in the averaging circuit that would otherwise occur if additional information were fed into an overloaded circuit. When the sheet leaves the test zone, it is marked with a grade according to the average voltage level that existed at the time the overload condition was reached.

Insufficient data indicating portion 528 includes a differential amplifier or comparator 532 which has its noninverting input connected to the denominator input of divider 390 and inverting input connected to a reference voltage supplying potentiometer 534. The output of comparator 532 appears on line 460 and is also connected through a 1 kilohm resistor 536 to a five volt dc supply so that the comparator output is at logic levels compatible with gates 444,448,452,456,458,474. Until the voltage at the denominator of divider 390 exceeds the reference voltage of potentiometer 534, a zero is transmitted on line 460. As previously explained, this prevents the operation of all of the grading relays except for the reject grade controlled by flip-flop 472. As each valid signal occurs, the voltage at the denominator input rises and for most sheets enough measurements will be made so that this voltage will exceed the reference voltage. Consequently, a one output normally appears on line 460 so that the grading relays operate as previously mentioned.

Overload indicator portion 530 includes a pair of differential amplifiers connected and used as voltage comparator 538, 540 having their outputs connected through respective 8.2 kilohm resistors 542, 544 to respective inputs of a NAND gate 546. The inputs of NAND gate 546 are also grounded through respective 1 kilohm resistors 548, 550. The inverting input of comparator 538 is fed from the output of signal integrator 384, which is the numerator input to divider 390. Similarly, the inverting input to comparator 540 is fed from the denominator input to divider 390. Both comparators 538, 540 have their noninverting inputs connected to a respective reference voltage supplying potentiometer 552, 554 connected to a fifteen volt dc supply.

Figures 9, 11:
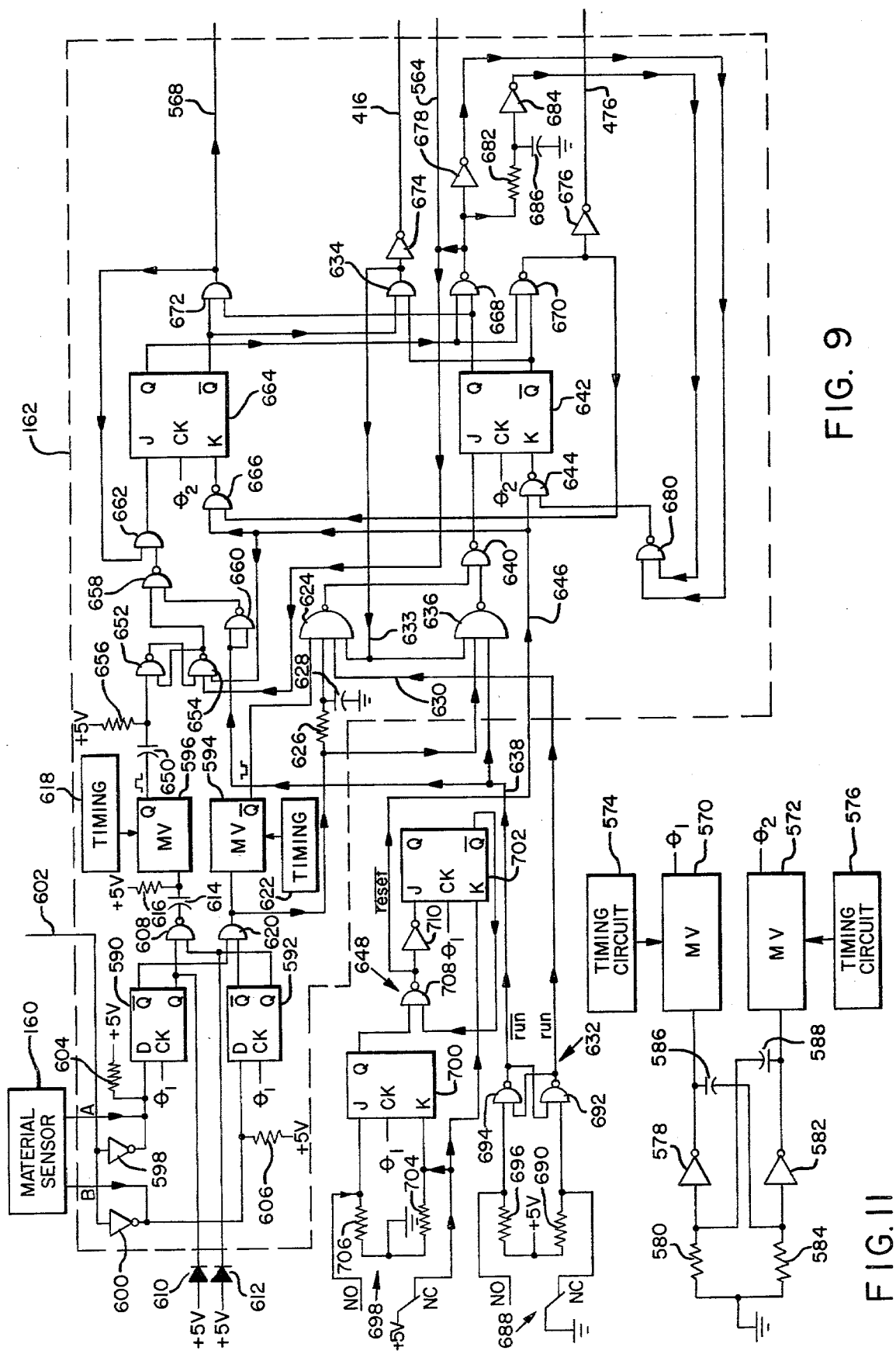
FIG. 9 is an electrical schematic diagram of the state sequencer circuit of FIG. 6.
FIG. 11 is a schematic diagram of a clocking circuit used in the circuit of FIG. 6.

Potentiometers 552, 554 are set at a voltage equal to the maximum level that does not overload the divider denominator and numerator circuits. Consequently, as long as those circuits are not overloaded, (i.e. their inputs haven't reached the reference voltage level) amplifiers 538, 540 each produce a logic one output. Therefore, gate 546 produces a logic zero output which is fed through an inverter 556 and appears as a logic one at an input of a NAND gate 558. The output of inverter 556 is also coupled through a 150 ohm resistor 560 to the cathode of a light emitting diode 562 which in turn has its anode connected to a five volt dc supply. During nonoverload conditions when the inverter 556 output is a logic one, diode 562 is off. NAND gate 558 also receives an input on a line 564 from state sequencer 162 (FIG. 9). This input is normally a logic one until a sheet leaves the test zone when it drops to logic zero.

Thus, during testing of a sheet, and under no overload conditions, the gate 558 output is a logic zero and is fed on line 532 to the valid test cycle discriminator 158 (FIG. 8). As explained more fully below in connection with this test cycle discriminator, when a zero appears on line 532, the output on line 418 from the discriminator is a logic one so that averaging continues. In contrast, if either the numerator or denominator circuits become overloaded, then a logic zero appears at one or both of the inputs of NAND gate 546 depending upon which of these circuits is overloaded. The resulting logic one output of gate 546 is inverted by inverter 556 and appears as a logic zero input to gate 558. Also, diode 562 lights up as it is forward biased under these conditions so that a visual indication of the overload condition is provided. Furthermore, a logic one output is produced from gate 558 on line 532. When this occurs, the output of valid test cycle discriminator 158 on line 418 goes to logic zero and prevents additional valid signal measurements from entering the averaging circuit. When the sheet leaves the test zone, the information contained in the averaging circuit at the time an overloaded condition was indicated is used to grade the sheet.

Although not all of the valid signals have been included in the average under such conditions, the results are sufficiently reliable for grading. Also, when the sheet leaves and integrator circuits 384, 386 of the averaging circuit are discharged, the overload indicating portion 530 returns to its nonoverload indicating state with a logic zero output at gate 558.

A digital voltmeter 565 is coupled to the output of divider 390 for monitoring this output when a veneer sheet leaves the test zone. As the veneer leaves the test zone, the signal on line 564 from the state sequencer goes negative and is coupled by a capacitor 559 as a negative pulse to the read control input of the digital voltmeter. This negative pulse causes the voltmeter to read the output of divider 390 and hence provides a visual indication of the veneer grade. Also, the negative pulse on line 564 causes the gate 558 output to go positive and reset the valid test cycle discriminator.

VALID TEST CYCLE DISCRIMINATOR

As shown in FIG. 8, valid test cycle discriminator 158 includes a JK flip-flop 566. The J input of this flip-flop is received on a line 568 from state sequencer 162, and as explained below, is positive while a sheet is in the test zone. The $\overline{ACO}$ output of inverter 273 is inverted by an inverter 570 and fed to the clocking input of flip-flop 566 so that clocking is synchronized with the ACO signals.

While the sheet is in the test zone, and when the divider 390 numerator and denominator circuits are not overloaded, the J and K inputs of flip-flop 566 are both logic ones so that its Q output on line 418 is a logic one.

Consequently, the output of gate 392 (FIG. 10) can go to zero when a valid signal is received and after the wait to add average time delay from circuit 156 is over. Therefore, new valid signal information can enter the averaging circuit. When the divider overloads, the K input of flip-flop 566 drops to a one and causes the Q output of the flip-flop to go to zero. When this happens, the gate 392 output is a logic one and additional data doesn't enter the averaging circuit.

In addition, when no sheet is in the test zone, the J input of the flip-flop is zero, as explained below, and the K input is a logic one. Therefore, the Q output of flip-flop 566 is a logic zero so that data can't enter the averaging circuit when a sheet is not present in the test zone.

STATE SEQUENCER

The state sequencer 162 is shown in FIG. 9 and performs several functions. In the first place, the state sequencer determines when a sheet of material is in the test zone and produces an indication of this fact on line 568 to valid test cycle discriminator 158 (FIG. 8). Furthermore, the state sequencer produces a clocking signal on line 476 to cause the logic levels on the D inputs of flip-flop 464,466,468,470,472,474 (FIG. 10) to be clocked through to their Q outputs after a sheet leaves the test zone. This clocking signal also controls spray head multivibrator 507 so that a grade mark is placed on the veneer. In addition, the state sequencer produces an output on line 416 to discharge or reset integrators 384, 386 of the averaging circuit after the veneer has left the test zone so as to prepare the integrators for testing of the next sheet. Also, the state sequencer produces the signal on the line 564 to the overload portion 530 of poor data detector 166 (FIG. 10) so that when no sheet is in the test zone, the K input to flip-flop 566 of the valid test cycle discriminator (FIG. 8), is a logic one. As mentioned above, the state sequencer output on line 564 also causes the digital voltmeter 565 to read the output of divider 390 (FIG. 10).

Clocking of state sequencer 162, and also of multivibrator 507 in the grade determination circuit 164 (FIG. 10), is accomplished by the clocking circuit shown in FIG. 11. This clocking circuit produces clocking pulse signals $\theta_1$ and $\theta_2$ of equal duration and which do not overlap in time. The clocking circuit includes a pair of multivibrators 570, 572 with conventional timing circuits 574, 576 for adjusting the duration of the clock pulses. The Q outputs of multivibrators 570, 572 respectively are the $\theta_1$ and $\theta_2$ clock pulses. The output of an inverter 578 is fed to the triggering input of multivibrator 570 and the input of this inverter is connected through a 2.7 kilohm resistor 580 to ground. Another inverter 582 is connected to the triggering input of multivibrator 572 and has its input connected through a 2.7 kilohm 584 to ground. The output of inverter 578 is coupled by a 0.22 microfarad capacitor 586 to the input of inverter 582. Similarly, the output of inverter 582 is coupled by a 0.22 microfarad capacitor 588 to the input of inverter 578.

The triggering network of resistors 580, 584, inverters 578, 582 and capacitors 586, 588 operate as an oscillator in a well known manner to alternately trigger the two multivibrators so as to produce the clocking pulses.

Although no set duration of the multivibrator output is required, the $\theta_1$ signal ends before the $\theta_2$ signal begins and the $\theta_2$ signal ends before the $\theta_1$ signal begins so that the signals don't overlap. For a specific example, these signals may be set at a one kilohertz frequency without the clocking pulses overlapping.

Returning to FIG. 9, state sequencer 162 includes a pair of D flip-flops 590, 592 which operate in response to the photo detectors of material sensor 160 for indicating when sheet material has been detected. One of these flip-flops is responsive to each photo detector and each photo detector must sense a sheet before the state sequencer considers a sheet to have been detected. Thus, when small pieces of scrap material are detected by one photo detector and not the other, the state sequencer does not produce a sheet indicating output on line 568.

The photo detectors are positioned a short distance upstream of the test zone. For this reason, a sheet will not enter the test zone until some time after detection by both photo detectors and will not leave the test zone until some time after the detectors stop sensing it. A one shot multivibrator 594 is provided to delay the operation of the state sequencer from the time a veneer sheet is first detected until the veneer reaches the test zone. Another one shot multivibrator 596 establishes a delay between the time veneer is no longer detected by the photodetectors and when it leaves the test zone.

The D input of flip-flop 590 is connected to the output of one of the photodetectors, labelled A, and also to the output of an open-collector inverter 598, for reasons explained below. The D input of flip-flop 592 is connected to the output of the other photo detector, labelled B, and also to the output of an open-collector inverter 600. The inputs of the inverters 598,600 are grounded by a line 602 through switch 130 so that their outputs are ones during veneer testing. On the other hand, inverters 598, 600 produce logic zero outputs when switch 130 is in its calibrate position so that the inverters override the photodetectors during calibration of the circuit. Thus, during calibration, state sequencer 12 behaves as if a sheet is being detected by the photodetector.

The D input to each flip-flop 590, 592 is connected through a respective 1 kilohm resistor 604, 606 to a 5 volt dc supply so that the photodetector outputs are at logic voltage levels suitable for the flip-flops. In addition, each flip-flop 590, 592 is clocked by the $\theta_1$ clocking signal.

The Q outputs of these flip-flops are fed to inputs of a respective NAND gate 608 and to the cathode of a respective light emitting diode 610, 612. The anodes of each of these diodes is connected to a five volt dc supply. Thus, whenever a logic zero appears at the D inputs of flip-flops 590,592, indicating the detection of a sheet, the Q outputs of these flip-flops go low and diodes 610, 612 light up. The output of NAND gate 608 is coupled through a 0.01 microfarad capacitor 614 to the triggering input of multivibrator 596. This triggering input is normally maintained at a positive voltage level by a five volt dc supply connected to it through a 10 kilohm resistor 616. However, when the output of gate 608 falls, at times when a photodetector no longer senses a sheet, a negative going spike is applied by capacitor 614 to the triggering input and causes a positive going signal at the Q output of this multivibrator. The Q output remains positive for a time established by a conventional timing circuit 618 and is set to allow sufficient time for a veneer sheet to leave the test zone after the photodetectors cease sensing it. This delay also makes the logic circuit insensitive to knot holes up to three inches in size. For example, with veneer moving on a conveyor at 200 feet per second, a typical operating speed, and the photodetectors about three inches upstream from the test zone, timing circuit 618 may conveniently be set to hold the Q output of multivibrator 618 positive for 70 milliseconds. With such a setting, the Q output goes negative when the sheet is ready to leave the test zone and causes the state sequencer, as explained below, to indicate that the sheet has left the test zone.

The $\overline{Q}$ outputs of D flip-flop 590,592 are fed to the inputs of an AND gate 620 which has its output connected to the triggering input of multivibrator 594. This multivibrator is triggered by the positive going edge of the output of gate 620 at the time both photodetectors first detect a sheet. When triggered, the $\overline{Q}$ output of multivibrator 594 produces a negative signal of a duration established by a timing circuit 622. The duration of this signal is adjustable according to the conveyor speed and is set to give the sheet time to travel into the test zone after it has been detected by the upstream photodetectors. A typical setting would be 100 millisecond for veneer travelling at 200 feet per second. The $\overline{Q}$ output of multivibrator 594 is fed to one input of a four input NAND gate 624 so that this gate produces a one output until after the multivibrator signal has ended. This indicates internally to the state sequencer that a sheet has not entered the test zone. The output of AND gate 620 is transmitted through a one kilohm resistor 626 to another input of NAND gate 624. This latter input is connected through a 0.01 microfarad capacitor 628 to ground. Capacitor 628 and resistor 626 delay the transmission of the output of gate 620 to NAND gate 624 until after the negative going output of multivibrator 594 has reached this NAND gate. Therefore, when no sheet is detected, the input to NAND gate 624 via resistor 626 is a zero and the NAND gate produces a one output indicating internally to the state sequencer that a sheet is not in the test zone. Furthermore, after the photodetectors sense a sheet, the output of NAND gate 624 remains a one until the zero signal from multivibrator 594 ends and the sheet passes into the test zone.

NAND gate 624 also receives an input on a line 630 from a run or testing indicating circuit 632. The signal on this line is a one unless the circuit is being calibrated in which case the signal is a zero. In addition, NAND gate 624 receives an input on a line 633 from an AND gate 634 for reasons apparent below. The circuit also includes a calibrate control NAND gate 636 which receives at its inputs the output of gate 620, the signal on line 633 and a signal on a line 638 from run circuit 632. During testing, the signal on line 638 is a logic zero so that the output of gate 636 is a one. On the other hand, during calibration the line 638 signal is a logic one so that the gate 636 output can be a one or a zero depending upon its other inputs. The outputs of NAND gate 624, 636 are connected to the inputs of a NAND gate 640 which in turn has its output connected to a J input of a JK flip-flop 642. The K input to this flip-flop is received from a NAND gate 644 which has one of its inputs connected by a line 646 to a reset circuit 648 operable as explained below.

Returning to multivibrator 596, its Q output is coupled through a 0.01 microfarad capacitor 650 to one input of a NAND gate 652. The output of gate 652 is connected to an input of another NAND gate 654. The capacitor 650 input of gate 652 is connected through a 10 kilohm resistor 656 to a five volt dc supply. This input to gate 652 is maintained at a one except that it goes to a zero at the falling edge of the multivibrator 596 Q output. The output of NAND gate 654 is connected to the other input of NAND gate 652, making these NAND gates a cross connected pair, and to an input of another NAND gate 658. The other input of NAND gate 658 is obtained at the output of a NAND gate 660. Gate 660 has both its inputs connected to line 638. During testing, because of the zero on line 638, the output of gate 660 is a one. An AND gate 662 receives an input from the output of gate 658 and has its output connected to the J input of a JK flip-flop 664. Flip-flop 664, like flip-flop 642 is clocked by the $\theta_2$ signals.

The K input of flip-flop 664 is obtained from the output of a NAND gate 666 with one of its inputs connected to line 646 and hence to reset circuit 648. The Q output of flip-flop 664 is fed to an input of each of a pair of NAND gates 668, 670. In addition the $\overline{Q}$ output of this flip-flop is fed to one input of an AND gate 672 and also to an input of an AND gate 634. Flip-flop 642 has its Q output fed to an input of gate 668 and an input of gate 672. The $\overline{Q}$ output of this flip-flop is fed to an input of gate 670 and also to an input of gate 634.

The output of gate 634 appears on line 633 and is also fed through an inverter 674. The inverter 674 output in turn is transmitted on line 416 to the averaging circuit 154 for controlling the discharge of the integrators 384, 386 (FIG. 10) within this circuit after the sheet leaves the test zone. The output of gate 672 is fed on line 568 to the valid signal discriminator 158 (FIG. 8) to indicate to the test cycle discriminator when a sheet is detected. Also, the gate 672 output is fed back to an input of gate 662.

The output of NAND gate 670 is fed to an input of NAND gate 666 and also through an inverter 676 to line 476 to provide a clocking signal for the grade determination circuit 164 (FIG. 10). As previously mentioned, this clocking signal causes the sheets to be marked as they leave the test zone.

The output of gate 668 is fed to an input of gate 654 and on line 564 to reset the valid test cycle discriminator flip-flop (FIG. 8) via gate 558 of the overload circuit 530 (FIG. 10). Also, the signal on line 564 causes digital voltmeter 565 to read the averaging circuit output at times when a sheet leaves the test zone.

The output of gate 668 is also fed through an inverter 678 to an input of a NAND gate 680 which has its output connected to an input of gate 644. In addition, the gate 668 output is fed through a 160 ohm resistor 682 and through an inverter 684 to another input of gate 680. A 100 microfarad capacitor 686 is connected between the input of inverter 684 and ground. Capacitor 686 and resistor 682 delay the transmittal of the signal from gate 668 to gate 680 for approximately 40 milliseconds. This gives the digital voltmeter time to read the divider 390 output prior to the discharge of the averaging circuit.

The operation of the state sequencer will be described with reference to Table 1 which lists the outputs of the various gates and circuit components of state sequencer 162

TABLE I

OUTPUTS OF SEQUENCER CIRCUIT ELEMENTS PRIOR TO DETECTION OF SHEET (INITIAL CONDITIONS)

| CIRCUIT ELEMENT | | OUTPUT | CIRCUIT ELEMENT | | OUTPUT | CIRCUIT ELEMENT | OUTPUT |
|---|---|---|---|---|---|---|---|
| FLIP FLOP 590 | Q | 1 | NAND GATE 644 | | 0 | AND GATE 634 | 1 |
| | $\overline{Q}$ | 0 | FLIP FLOP 642 | Q | 0 | AND GATE 672 | 0 |
| FLIP FLOP 592 | Q | 1 | | $\overline{Q}$ | 1 | NAND GATE 668 | 1 |
| | $\overline{Q}$ | 0 | NAND GATE 652 | | 0 | NAND GATE 670 | 1 |
| NAND GATE 608 | | 0 | NAND GATE 654 | | 1 | INVERTER 674 | 0 |
| AND GATE 620 | | 0 | NAND GATE 658 | | 0 | INVERTER 678 | 0 |
| MULTIVIBRATOR 594 | $\overline{Q}$ | 1 | NAND GATE 660 | | 1 | NAND GATE 680 | 1 |
| MULTIVIBRATOR 596 | Q | 0 | AND GATE 662 | | 0 | INVERTER 676 | 0 |
| NAND GATE 624 | | 1 | NAND GATE 666 | | 0 | INVERTER 684 | 0 |
| NAND GATE 636 | | 1 | FLIP FLOP 664 | Q | 0 | LINE 630 | 1 |
| NAND GATE 640 | | 0 | | $\overline{Q}$ | 1 | LINE 638 | 0 |
| | | | | | | LINE 646 | 1 | under initial conditions. Initial conditions mean the steady state conditions of the elements prior to the detection of a sheet of material. To illustrate how this table operates, when neither photodetector senses the presence of a veneer sheet, the A and B outputs of the material sensor are logic ones. Consequently, the Q outputs of flip-flops 590, 592 are high and the $\overline{Q}$ outputs are zeroes. These conditions are shown in the output column adjacent to the flip-flop 590, 592 listings. Because the Q outputs of D flip-flops 590,592 are both high, NAND gate 608 produces a zero output indicated by the zero in the output column adjacent to gate 608. Furthermore, because of capacitor 614 and pull up resistor 616, the input to multivibrator 596 is a steady logic one so that its Q output is zero. In a like manner, by looking at the output column of Table I, the initial condition logic level of the output of each element can be determined.

When the photodetectors both detect the presence of veneer, the D inputs to flip-flops 590, 592 go to zero. Therefore, the Q outputs of these flip-flops go to zero coincident with the $\theta_1$ clock pulse and the $\overline{Q}$ outputs go to one. Because its inputs are zero, NAND gate 608 produces a one output to multivibrator 596. However, as this multivibrator is only triggered by a negative going transition, its Q output remains zero. At the same time, the output of gate 620 goes positive to a logic one and triggers multivibrator 594 to produce a negative pulse at its $\overline{Q}$ output. The output from gate 620, after being delayed by resistor 626 and capacito4r 628, reaches NAND gate 624. However, this NAND gate continues to produce a one output as it has a zero input from multivibrator 594. At the end of multivibrator 594 signal, when the veneer sheet enters the test zone, all of the inputs of NAND gate 624 are ones. Therefore, the output of this gate goes to zero. This in turn causes NAND gate 640 to produce a one output to the J input of flip-flop 642.

Upon the occurrence of the first $\theta_2$ clocking signal following the time that gate 640 produces a positive output, flip-flop 642 changes state. That is, its Q output goes to one and its $\overline{Q}$ output goes to zero. Consequently, the output of AND gate 634 goes to zero, thereby causing the gate 624 output to again go to one. This change in NAND gate 624, in turn, causes NAND gate 640 to again produce a zero output. In addition, the outputs of AND gate 672 and of inverter 674 go to one. This logic one output of gate 672 is transmitted on line 568 to the valid cycle test discriminator 158 (FIG. 8) and indicates that a sheet is in the test zone. Also, the positive output of inverter 674 is transmitted on line 416 to open the discharge switches 412, 414 of the averaging circuit so that integrating circuits 384, 386 are ready to receive new data.

The state sequencer remains in this state until the veneer leaves the test zone at which time neither photodetector will sense the sheet. When this occurs, the Q outputs of flip-flops 590, 592 go positive while their $\overline{Q}$ outputs go to zero. Therefore, both NAND gate 608 and AND gate 620 produce zero outputs. As multivibrator 594 is triggered by a positive voltage transition, its Q output remains unchanged even though the gate 620 output goes low. However, when the gate 608 output goes low, a negative spike is applied to the triggering input of multivibrator 596 causing it to produce a positive signal. This positive signal has no effect on the positive logic level at the input of NAND gate 652. But, at the end of the multivibrator 596 signal when its level falls to zero thereby indicating the sheet material has left the text zone, a negative pulse is applied to the input of NAND gate 652. As a result, NAND gate 652 produces one output which causes the output of NAND gate 654 to become zero. This causes the NAND gate 658 output to go high. When NAND gate 658 goes high, the output of AND gate 662 goes to one so that a positive signal is applied to the J input of flip-flop 664.

Upon the occurrence of the next $\theta_2$ clocking signal, flip-flop 664 changes states, with its Q output going to a logic one and its $\overline{Q}$ output going to zero. The drop in the $\overline{Q}$ output causes AND gate 672 to produce a zero output to the valid test cycle discriminator 158 (FIG. 8) to indicate that the veneer has left the test zone. In addition, the $\overline{Q}$ output is fed to one input of AND gate 634, but the output of this AND gate remains unchanged because it is already receiving a zero from the $\overline{Q}$ output of flip-flop 642.

Because gate 668 is now receiving positive inputs from both flip-flops 664 and 642, its output is a zero and is transmitted on line 564 causing voltmeter 565 (FIG. 10) to read the divider 390 output. Also, the zero from gate 668 causes gate 654 to produce a positive output, which in turn causes gates 652 and 658 to produce zero outputs. The output of gate 662 remains unchanged at zero because it is already receiving a zero from gate 672. Additionally, the inverted gate 668 output, a positive signal, is fed by inverter 678 to one input of NAND gate 680.

Next, the zero output from gate 668, having been delayed by resistor 682 and capacitor 686 to allow the voltmeter to read the divider 390 output, reaches the input of inverter 684 so that its output goes to one. Consequently, the gate 680 output becomes zero and a positive output is applied by gate 644 to the K input of flip-flop 642.

Upon the occurrence of the next $\theta_2$ clocking pulse, flip-flop 642 changes states with its Q output becoming zero and its $\overline{Q}$ output going to one. With this change in states, the output of gate 668 goes positive, of inverter 678 goes to zero, of gate 680 goes to one and of gate 644 goes to zero. In addition, the output of gate 670 goes to zero so that the outputs of gate 666 and inverter 676 become ones. The positive output from inverter 676 is fed on line 476 to the grade determination circuit 164 (FIG. 10) for control of the sheet marking circuit 28.

At the next $\theta_2$ clocking signal, because a one is being applied to its K input and a zero to its J input, flip-flop 664 changes states with its Q input going to zero and its $\overline{Q}$ input going to a one. With this $\overline{Q}$ a one, AND gate 634 sends a one output on line 632 to NAND gate 624. Furthermore, the inverted output of AND gate 634 is transmitted on line 416 from inverter 674 to averaging circuit 154 and causes the integrators of the averaging circuit to discharge prior to the detection of the next sheet of veneer. In addition, because of the zero Q output of flip-flop 664, the gate 670 output goes to a logic one and causes gate 666 to produce a zero at the K input of flip-flop 664. In addition, the inverter 676 output goes to zero to block clocking of information from the grade determination circuit to the sheet marking circuit until the next sheet has been tested.

Finally, approximately forty milliseconds after the output of gate 668 when positive, the inverter 684 output goes to zero so that the circuitry is again back in its initial conditions awaiting the next sheet.

Assuming for the moment that a small piece of scrap veneer passed by and was detected only by the photodetector producing output A. In this event, the D input of flip-flop 590 goes low while the D input to flip-flop 592 remains high. Consequently, gate 620 continues to produce a low output and multivibrator 594 is not triggered. However, the output of gate 608 goes low and triggers multivibrator 596. At the end of this multivibrator 596 signal, the gate 652 output would go high, the gate 654 output would go low, and the gate 658 output would go high. However, the gate 662 output remains low because its input from gate 672 is still low. Thereafter, at the end of the multivibrator 596 output, the circuitry reestablishes its initial conditions. Thus, detection of material by this photo detector alone does not trigger the averaging of data into the averaging circuit.

Similarly, the detection of scrap material by detector B alone does not start the circuitry operating. In such case, the Q output of multivibrator 592 would go low, while its $\overline{Q}$ output would go high. However, gate 620 output remains zero because the $\overline{Q}$ output of flip-flop 590 is still low. However, because of the change in the Q output of multivibrator 592, the gate 608 output goes high. When the detection of the scrap material by detector B ends, the output of gate 608 goes low and triggers multivibrator 596. However, in the same manner as explained above in connection with detection of scrap material only by detector A, this change does not cause averaging of ultrasonic travel delay times to begin.

In a like manner, after both detectors sense the presence of sheet material and averaging has begun, averaging continues until both detectors no longer sense the material.

The run mode indication circuit 632 includes a switch 688 with which one of two lines may be selectively grounded. It is set to its normally closed (NC) position, during testing of veneer. The NC switch position is connected through a 1 kilohm resistor 690 to a five volt dc supply and to an input of a NAND gate 692. The output of gate 692 is connected to an input of a NAND gate 694 and also by line 630 to NAND gate 624. The five volt dc supply is also fed through another 1 kilohm resistor 696 to another input of NAND gate 694 and the normally open switch position, NO, is also connected to this input. The output of gate 694 is fed on line 638 to gates 636, 660. During testing of veneer, the output of gate 692 is a one and of gate 694 is a zero. In contrast, during calibration of the circuit, switch 688 is moved to its normally open position. Under these conditions, the gate 694 output is a one and the gate 692 output is a zero. The outputs of gate 692, 694 are used internally within the state sequencer for indicating whether testing or calibration is being accomplished.

The reset circuit 648 in FIG. 9 includes a switch 698 connected at one side to a positive five volt dc supply. Its other side, is shown in its normally closed position, NC, which couples five volt dc supply to the K inputs of two JK flip-flops 700, 702. The K input of each flip-flop 700, 702 is grounded through a common 270 ohm resistor 704. The open circuited, normally open switch position, NO, is connected to the J input of flip-flop 700 and is grounded through another 270 ohm resistor 706. Flip-flops 700, 702 are both clocked by the $\theta_1$ clocking signal.

The Q output of flip-flop 700 is connected to one input of a NAND gate 708 whose output is transmitted through an inverter 710 to the J input of flip-flop 702. The $\overline{\text{reset}}$ signal on line 646 is taken from the output of NAND gate 708. The Q output of flip-flop 702 is connected back to the other input of NAND gate 708. With the above connections, the Q output of flip-flop 700 is a zero, the $\overline{\text{reset}}$ signal from gate 708 is a one, and the $\overline{Q}$ output of flip-flop 702 is a one. Whenever the reset switch 698 is moved to its normally open position, the Q output of flip-flop 700 goes positive coincident with clock $\theta_1$, and causes the output of gate 708 to go to zero and remain a zero until the next succeeding $\theta_1$ clock signal. This in turn causes the outputs of gate 644, 666 to go to ones and forces the outputs of flip-flops 642, 664 to their initial states coincident with the $\theta_2$ clock signal between the start and comcompletion of the reset signal.

CALIBRATION SIGNAL GENERATOR

The calibration signal generator 170, shown in FIG. 8 is designed to generate a signal of a known time length. This signal is used in the adjustment of the potentiometers of grade threshold circuit 164 to activate a spray head to grade the sheet with a grade corresponding to average travel times of a duration equal to the duration of the signal produced by this generator. The time duration of the generator output is variable so that after a grade threshold for one spray head bas been established, the generator 170 output signal can be varied and used to calibrate the threshold for the next spray head, etc. In this manner, each spray head can be set to mark veneer with desired grade marks corresponding to a selected average travel time for the grade.

Calibrator signal generator 170 includes a potentiometer 712 supplied by a ten volt dc voltage and with its wiper arm connected to the noninverting input of a voltage follower amplifier 714. Feedback from the output of this amplifier is transmitted to its inverting input. The amplifier 714 output is fed through a 10 kilohm resistor 716 to the noninverting input of an amplifier 718 included in a ramp generator portion of the calibration circuit. The output of amplifier 718 is fed through a 10 kilohm feedback resistor 720 to the inverting input of this amplifier and this latter input is also connected through another 10 kilohm resistor 722 to ground. In addition, the output of amplifier 718 is connected to one side of a 10 kilohm resistor 724. The other side of resistor 724 is connected to one side of a 0.15 microfarad capacitor 726 having its other side grounded, and to the noninverting input of amplifier 718, and to the collector of an NPN transistor 728. The emitter of transistor 728 is grounded.

The output of amplifier 718 is fed to the noninverting input of a differential comparator 730 having its output connected through an inverter 732 to an input of a NAND gate 734. The output of amplifier 730 is also connected through a 4.7 kilohm resistor 736 to a five volt dc supply so that its level is compatible with the logic levels required to operate inverter 732. The inverting input of comparator 730 is coupled by a 0.22 microfarad capacitor 736 to ground and also to a potentiometer 738 supplied by a ten volt dc supply. One input of NAND gate 734 is connected to an enable, disable section of switch 130. In its illustrated disable position, switch 130 supplies a zero to one input of gate 734 fixing the output of this gate at a one and thus disabling the calibrator circuit. When in its enable position, during calibration, a five volt dc supply is connected to this input of gate 734 so that its output may be a zero or a one depending on its other inputs. The output of gate 734 is connected through a 1 kilohm resistor 742 to the base of transistor 728 and also to the input of a NAND gate 744. The output of NAND gate 744 is connected to another input of NAND gate 734 and is coupled through a 0.1 microfarad capacitor 746 to one side of a 3.9 kilohm resistor 748. The other side of resistor 748 is connected through a 1 kilohm resistor 750 to ground and is connected by a line 752 to a calibrate signal input of test switch 130. A triggering signal on line 375 from delay to start circuit 152 is fed through an inverter 754 to another input of NAND gate 744.

The calibrator generator circuit operates as follows. Switch 130 is turned to its enable position, opposite of position shown. Upon receipt of a triggering signal on line 375, the output of gate 744 goes to a logic one. Consequently, a positive voltage spike appears on the line 752 and is fed through the switch 130, which has been moved to its calibrate position, to the signal threshold detector 132. At the same time, a zero output is produced by gate 734 and causes transistor 728 to turn off. With transistor 728 off, the feedback loop through resistor 724 is no longer shorted by the transistor so that the output of amplifier 718 rises as capacitor 726 charges in a linear ramp voltage. Eventually, when the output of amplifier 718 exceeds the reference voltage at the noninverting input of comparator 730, the output of this latter comparator goes positive. As a result, the inverted output of comparator 730, a zero, is applied by inverter 732 to gate 734 and causes the gate 734 output to go to a logic one. When this occurs, transistor 728 again turns on so that compacitor 726 discharges. At the same time, a negative going voltage spike is fed on line 752 to the signal threshold detector. The time between the positive going spike on line 752 and the negative going spike is established by adjusting the wiper arms of potentiometers 712, 738 and can be set at a known level. As a result, a signal of a known time duration is produced by the calibrator signal generator and can be used in setting the grade thresholds.

When in its calibrate mode, test switch 130 supplies a logic one voltage to the inputs of inverters 598, 600 (FIG. 9) so that they produce logic zero outputs to their respective D flip-flops 590, 592. The zero outputs of these inverters override the signal from the photodetectors so that the state sequencer operates as if a sheet is in the test zone.

OVERALL OPERATION OF THE DEVICE

Veneer passing along a conveyor is detected by a pair of photodetectors in material sensor 160 positioned upstream of a test zone between the rolling transducers 10, 16. After a delay to allow the veneer to travel into the test zone, the state sequencer enables a valid test cycle discriminator so that the circuit is ready to receive data. Transmitter 12 causes the generation of the repetitive ultrasonic signals by rolling transducer 10 through the sheet material.

These ultrasonic signals are picked up by rolling transducer 16, and hence by a receiver 18, and are fed to a signal threshold detector 132. Signals that exceed the minimum threshold level set by detector 132 produce a signal to a valid signal detector 136. In addition, the receiver 18 output is tested by a noise discriminator 134 and if it is above a noise threshold, an invalid signal is sent to detector 136. A time window circuit including a pair of range gates 142, 144 establish a minimum and maximum allowable travel time for valid signals. The range gates are connected to detector 136 so that signals having travel times not within this maximum and minimum are disregarded as invalid. Only those detected signals which exceed the threshold set by detector 132, are not noise as determined by noise discriminator 134, and which are within the time window established by time window circuit 146, are evaluated by valid signal detector 136 to be valid.

Upon receipt of a valid signal, detector 136 sends a valid test signal to an elapsed time integrator 150. This latter circuit produces a rising ramp voltage output beginning after a delay established by a relay to start ETI circuit 152. When the elapsed time integrator receives the valid test signal, it holds its output at the voltage it had reached at the time of the valid test signal. After the end of a delay established by wait to add average circuit 156, designed to insure that each valid test signal is given equal weight when averaged, the elapsed time integrator output enters averaging circuit 154. Averaging circuit 154 integrates the elapsed time integrator output to compute the average of the valid test signals for a sheet. Hence, the averaging circuit determines an average travel time for ultrasonic signals to pass through the veneer.

After the veneer leaves the test zone, state sequencer 162 causes the averaging circuit to produce a voltage output representing the average to grade determination circuit 164. The grade determination circuit in turn causes the sheet to be marked with a grade corresponding to the average travel time. In this manner, veneer moving along a conveyor is automatically and reliably graded.

It will be appreciated that any or all of the various functions performed by the testing circuitry as herein described can be likewise implemented employing general or special purpose digital computers, and/or microprocessors, and digital timers. The programming of such devices to carry out the sequencing and other setting operations described above is straightforward. In such cases, the computer elements perform in an equivalent manner to the circuitry herein disclosed.

Having illustrated and described the principles of my invention with reference to one preferred embodiment, it should be apparent to those persons skilled in the art that such invention may be modified in arrangement and detail without departing from such principles. I claim as my invention all such modifications as come within the true spirit and scope of the following claims.

I claim:

1. A rolling apparatus for ultrasonic testing of sheet material which couples ultrasonic signals in either direction between a focusing surface of a transducer and the plane of the sheet, comprising:
   wheel support means;
   wheel means mounted to said wheel support means for rotation about the axis of said wheel means, said wheel means defining an interior transducer chamber for receiving the transducer and including a rim having a cylindrical contact surface for rolling in contact with the sheet;
   focusing means projecting inwardly into said transducer chamber from said contact surface for transmitting said ultrasonic signals in said either direction between the transducer focusing surface and plane of the sheet;
   said focusing means comprising an annular focusing ring which rotates about the axis of said wheel means with the rolling of said rim.

2. An apparatus according to claim 1 in which said focusing ring has a frustoconical ring focusing surface operatively positioned for moving past the transducer focusing surface during rolling of the rim, and in which the portion of said ring focusing surface passing the transducer focusing surface couples ultrasonic signals therethrough and between the transducer and the plane of the sheet.

3. An apparatus according to claim 2 in which said focusing ring means is of right triangular cross section with a hypotenuse parallel to the upper surface of the sheet and a base positioned in the ring focusing surface and generally perpendicular to the transducer focusing surface so that the primary direction of travel of ultrasonic signals through the focusing ring is in a direction generally perpendicular to the ring focusing surface.

4. An apparatus according to claim 3 in which the angle between the hypotenuse and the base is in the range of from fifty to seventy degrees so that the angle of incidence between the primary direction of travel of ultrasonic signals through the focusing ring and line normal to the upper surface of the sheet is in the range of from fifty to seventy degrees, and in which said focusing rings is of a material through which ultrasonic waves travel at a rate slower than the rate of travel through the sheet.

5. an apparatus according to claim 4 in which the angle of incidence between the primary direction of travel of ultrasonic signals through the focusing ring and a line normal to upper surface of the sheet is sixty degrees and the focusing ring is of aluminum.

6. An apparatus according to claim 1 in which said rim includes a cylindrical recessed rim portion of lesser diameter than the diameter of the cylindrical contact surface so as to remain spaced from the sheet during rolling of the rim to thereby reduce the transmission of undesirable signals between the transducer and the sheet.

7. A rolling apparatus for ultrasonic testing of sheet material comprising:
   a stationary shaft;
   a wheel mounted to said shaft for rotation about the axis of said wheel, said wheel defining an interior transducer chamber and including a rim having a cylindrical contact surface with a contacting portion rolling in contact with the sheet;
   an ultrasonic transducer rigidly mounted to said shaft within said transducer chamber and oriented with a transducer focusing surface for directing ultrasonic energy toward said contacting portion;
   an annular focusing ring projecting inwardly into said transducer chamber from said contact surface and which rotates about the axis of the wheel with the rolling of the rim, said focusing ring including a frustoconical focusing ring surface which continuously moves past the transducer focusing surface with the rolling, said transducer surface and said ring coupling surface being spaced apart so as to provide a gap therebetween, and in which at least a portion of said focusing ring surface is positioned between said transducer surface and contacting portion for coupling ultrasonic signals in either direction between the transducer focusing surface and the plane of the sheet; and
   a coupling oil within said transducer chamber for filling the said gap to facilitate coupling of ultrasonic signals between the transducer coupling surface and ring focusing surface.

8. An apparatus according to claim 7 including a transformer positioned within said transducer chamber for applying voltage pulses to said transducer to cause said transducer to gnerate ultrasonic signals, and in which said oil has been treated by outgassing so as to reduce cavitation of the oil in the gap.

9. An apparatus according to claim 8 in which said shaft is provided with a passageway extending from one of its ends, along its axis, and to the transducer chamber for passage of electrical cable therethrough and to said transformer.

10. An apparatus according to claim 8 which includes a collar keyed to said shaft and an angle bracket mounted to said collar and connected to said transducer for rigidly mounting said transducer in a preselected orientation.

11. An apparatus according to claim 7 in which said transducer focusing surface includes a coating of an ultrasonic conducting material which conforms the transducer focusing surface to the curvature of the ring focusing surface so to thereby provide a gap of uniform width.

12. An apparatus according to claim 7 in which said rim defines an annular transducer receiving notch bounded on one side by said ring focusing surface and at its other side by frustoconical surface generally perpendicular to said ring focusing surface.

13. An apparatus for ultrasonically testing sheet material comprising:
rolling transducer transmitter means for generating ultrasonic signals and for introducing the generated signals into the sheet material in a test zone for travel generally in the plane of the sheet;
rolling transducer detector means spaced apart from said transmitter means for detecting ultrasonic signals travelling in the plane of the sheet in the test zone;
timing circuit means for generating travel time signals representing the travel time taken by ultrasonic signals to travel in the sheet from said transmitter means to said detector means;
averaging circuit means for averaging a plurality of said time signals for the sheet and for producing an average travel time signal for the sheet representing an average of the travel time signals and thereby an average travel time for the sheet;
grading circuit means responsive to said average travel time signal for producing an indication of a grade corresponding to the average travel time for the sheet.

14. An apparatus according to claim 13 in which said detector means produces detector output signals of an amplitude corresponding to the amplitude of ultrasonic signals detected by said detector means;
said timing circuit means including signal discriminator means for producing a valid signal indication of those detector output signals of amplitudes within a preselected minimum and maximum amplitude range;
said timing circuit means including a timer circuit for generating time signals representing only travel times of ultrasonic signals which caused the production of said valid signal indications.

15. An apparatus according to claim 14 including time window circuit means for establishing a preselected minimum and maximum expected travel time for ultrasonic signals to pass from said transmitter means to said detector means, and for blocking said timer circuit means from generating time signals not within said minimum and maximum expected travel times.

16. An apparatus according to claim 13 in which said detector means produces a detector output voltage of an amplitude corresponding to the amplitude of each signal detected by said detector means;
said timing circuit means including means for generating a synchronization signal synchronized with the generation of each ultrasonic signal, signal threshold detector means for comparing the amplitude of the detector output voltage with the amplitude of a reference voltage and for producing a valid threshold signal indication output when the detector output voltage exceeds the reference voltage, noise discriminator means for comparing the amplitude of the detector output voltage with the amplitude of a noise reference voltage and for producing a noise signal indication output when the detector output voltage is greater than the noise reference voltage, time window circuit means including first and second range gates, said first range gate comprising means for producing a minimum travel time signal at the end of a minimum expected travel time of each ultrasonic signal measured from its associated synchronization signal and said second range gate comprising means for producing a maximum travel time signal at the end of a maximum expected travel time for each ultrasonic signal measured from its associated synchronization signal;
said timing circuit means also including valid signal detector means having inputs coupled to an output of said threshold detector means, an output of said noise discriminator means, an output of said first range gate and an output of said second range gate, said valid signal detector means comprising means for producing valid test signal outputs upon each first occurrence of a valid threshold signal indication output following a synchronizing signal, and which occurs between said minimum and maximum expected travel times, and which occurs without there having been a noise signal indication output between the synchronization signal and said first occurrence;
and in which said timing circuit also includes a timer circuit for generating time signals representing only travel times of ultrasonic signals which caused the generation of said valid test signal outputs.

17. An apparatus according to claim 16 in which said noise discriminator means includes variable noise level circuit means for varying the amplitude of the noise reference voltage as a function of time from the generation of each synchronization signal.

18. An apparatus according to claim 17 in which said variable noise level circuit means operates in response to said each synchronization signal to produce a first noise reference voltage upon the occurrence of said each synchornization signal, said variable noise level circuit means having an input coupled to an output of said first range gate, said first range gate including means for producing a noise reference triggering output signal to said variable noise level circuit means at the end of each minimum expected travel time, and in which said variable noise level circuit means comprises means for producing a second noise reference voltage of an amplitude greater than said first noise reference voltage in response to said noise reference triggering output signal.

19. An apparatus according to claim 16 in which said timer circuit comprises an elapsed time integrator circuit including ramp voltage generator means having an input coupled to an output of said signal detector means and an output coupled to said averaging circuit means, said timer circuit also including means for resetting the output of said ramp voltage generator means to a first voltage level following the end of each synchronization signal, said ramp voltage generator means comprising means for producing a ramp voltage starting from said first voltage level at a preselected starting time from each synchronization signal, said elapsed time integrator means also including means responsive to said valid test signal output signals for causing said ramp generator means to hold its output at the voltage level reached at the time a valid test signal output is generated until said ramp generator means is reset, whereby the output of said ramp generator means represents the travel time of said ultrasonic signals.

20. An apparatus according to claim 19 including delay to start elapsed time integrator means for delaying the starting time of said ramp generator means a preselected delay time from each synchronizing signal, said delay time being generally equivalent to the time for said ultrasonic signals to pass from said transmitter means and into the sheet and from the sheet through said detector means to said signal threshold detector means so that said travel time signals represent time spent by ultrasonic signals travelling in the sheet.

21. An apparatus according to claim 19 in which said averaging circuit includes wait to add average circuit means for delaying the entry of the output of said ramp generator means into said averaging circuit means until a time after the end of said maximum expected travel time.

22. An apparatus according to claim 16 in which said grading circuit means includes means for controlling a plurality of grade spray heads so as to cause the spray heads to spray a grade mark on the sheet representing the average travel time for the sheet.

23. An apparatus according to claim 16 including material sensor means for detecting the presence of sheet material, state sequencer means coupled to said material sensor means for producing a sheet test output signal when a sheet is in the test zone, valid test cycle discriminator means coupled to said sequencer means for receiving said sheet test output signal and for blocking the entry of travel time signals from timing circuit means into said averaging circuit means when sheets are not in the test zone.

24. An apparatus according to claim 23 which includes poor data detector means for producing an overload output signal when said averaging circuit means becomes overloaded, said test cycle discriminator means being coupled to said poor data detector means for blocking the entry of travel time signals output into said averaging circuit means at times when said overload output signal is produced.

25. An apparatus according to claim 24 in which said poor data detector means includes insufficient data detecting means for determining when said averaging circuit means has not received sufficient travel time signals for a sheet to provide an average time signal of sufficient reliability for use in grading the sheet.

26. An apparatus according to claim 13 in which said state sequencer means includes means for causing said grade determination circuit means to receive each average time signal from said averaging circuit means and for resetting said averaging circuit means when a sheet leaves the test zone.

27. An apparatus according to claim 16 including calibration signal generator means for producing output signals of known and adjustable time lengths, switching means for coupling said calibration signal generator output signals to said signal threshold detector means and for simultaneously blocking the passage of signals from said detector means to said signal threshold detector means, whereby with said calibration signals set at one time interval said grade determination can be adjusted to produce a grade indication corresponding to travel times equal to said one time interval and with said calibration signals set at another time interval said grade determination circuit can be adjusted to produce a grade indication corresponding to travel times equal to said another time interval.

28. An apparatus for ultrasonically testing sheets of wood veneer moving on a conveyor comprising:
a rolling transducer transmitter for rolling in contact with the veneer and for introducing ultrasonic signals into the veneer for travel with the grain of the veneer through a test zone;
a rolling transducer receiver spaced apart from said transmitter for rolling in contact with the veneer and for detecting ultrasonic signals travelling with the grain of the veneer through the test zone;
testing circuit means coupled to said transmitter and to said receiver for measuring the travel time taken by ultrasonic signals to travel through the test zone, said testing circuit means, including means for producing an average travel time output signal representing the average of a plurality of said travel times; and
grading circuit means coupled to said testing circuit means for marking the veneer with a grade indication corresponding to the average travel time signal.

* * * * *